United States Patent
Fateh et al.

(10) Patent No.: US 10,617,605 B2
(45) Date of Patent: Apr. 14, 2020

(54) METHOD AND APPARATUS FOR SMART MEDICATION AUTHENTICATION THROUGH CONSIDERING NON-SMART INCIDENTAL MATERIALS

(71) Applicant: Kali Care, Inc., Mountain View, CA (US)

(72) Inventors: Sina Fateh, Sunnyvale, CA (US); Philippe Cailloux, Sunnyvale, CA (US); Navid Nick Afsarifard, Atherton, CA (US); Abhijit Kalamkar, Sunnyvale, CA (US); Michael Lamberty, San Jose, CA (US)

(73) Assignee: KALI CARE, INC., Santa Clara, CA (US)

( * ) Notice: Subject to any disclaimer, the term of this patent is extended or adjusted under 35 U.S.C. 154(b) by 0 days.

(21) Appl. No.: 16/238,905

(22) Filed: Jan. 3, 2019

(65) Prior Publication Data

US 2019/0209433 A1 Jul. 11, 2019

Related U.S. Application Data

(60) Provisional application No. 62/614,194, filed on Jan. 5, 2018.

(51) Int. Cl.
*A61J 1/18* (2006.01)
*G08B 21/24* (2006.01)
(Continued)

(52) U.S. Cl.
CPC ............... *A61J 1/18* (2013.01); *A61F 9/0008* (2013.01); *A61J 1/16* (2013.01); *G08B 21/24* (2013.01);
(Continued)

(58) Field of Classification Search
CPC ...... A61J 1/18; A61J 2200/30; A61J 2200/70; G08B 21/24; A61F 9/0008; A61F 2200/74; A61B 50/36
(Continued)

(56) References Cited

U.S. PATENT DOCUMENTS 4,419,016 A * 12/1983 Zoltan .................. A61J 7/0481
368/10
8,226,610 B2 * 7/2012 Edwards ................. A61M 5/19
604/137
(Continued)

*Primary Examiner* — John A Tweel, Jr.
(74) *Attorney, Agent, or Firm* — Perkins Coie LLP

(57) ABSTRACT

Arrangements are provided for "smart" functionality such as for tracking medication use to determine adherence, without requiring smart containers therefor. A bin is provided for receiving used/empty containers, packaging, or other discarded material incidental to the use of the medication. Sensors generate signals when the material is deposited within the bin, and a processor determines whether those signals correspond with the incidental material of interest. The processor also may identify when signals correspond with other, spurious material deposited in the bin. Responsive to a positive correspondence, a contextual event such as deposition of a used vial is stored, displayed, communicated, and/or otherwise registered. Contextual events, times therefor, lack of same, etc. are considered to provide authenticated determinations of adherence to a medication regimen. Authenticated adherence determinations may support medication adherence monitoring, medication adherence itself, and/or medication outcomes for patient treatment, clinical trials, etc.

25 Claims, 18 Drawing Sheets

(51) Int. Cl.
*A61F 9/00* (2006.01)
*A61J 1/16* (2006.01)
*B09B 3/00* (2006.01)
*A61B 50/36* (2016.01)

(52) U.S. Cl.
CPC .......... *A61B 50/36* (2016.02); *A61J 2200/30* (2013.01); *A61J 2200/70* (2013.01); *A61J 2200/74* (2013.01); *B09B 3/0075* (2013.01)

(58) Field of Classification Search
USPC ..................................................... 340/568.1
See application file for complete search history.

(56) References Cited

U.S. PATENT DOCUMENTS

| | | | |
|---|---|---|---|
| 9,358,499 B2* | 6/2016 | Akdogan | A61J 7/0076 |
| 9,775,780 B2* | 10/2017 | Afsarifard | A61J 7/0418 |
| 9,839,391 B2* | 12/2017 | Eaton | A61F 9/0008 |
| 10,026,296 B2* | 7/2018 | Fateh | A45D 40/0068 |
| 2013/0195326 A1* | 8/2013 | Bear | G06F 19/3456 |
| | | | 382/128 |
| 2015/0232256 A1 | 8/2015 | Hoover et al. | |
| 2016/0030673 A1 | 2/2016 | White et al. | |
| 2017/0231867 A1* | 8/2017 | Maston | A61J 1/03 |
| | | | 206/534 |
| 2017/0270774 A1 | 9/2017 | Fateh et al. | |
| 2019/0103179 A1* | 4/2019 | Fateh | G16H 20/13 |
| 2019/0144174 A1* | 5/2019 | Chang | B65D 47/18 |
| | | | 604/295 |
| 2019/0233185 A1* | 8/2019 | Strong | B65D 41/0471 |

* cited by examiner

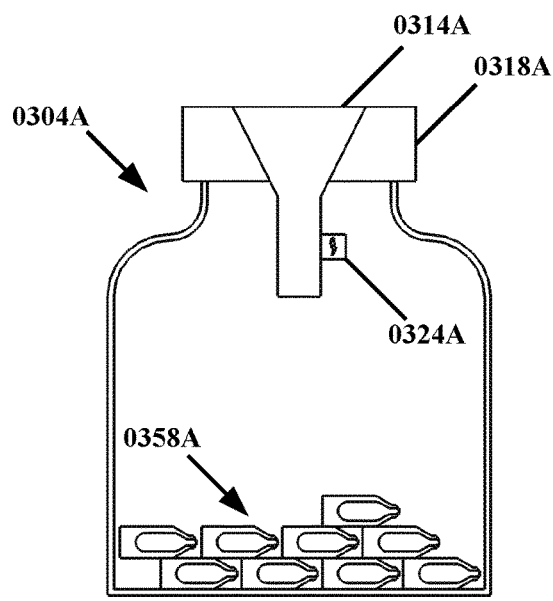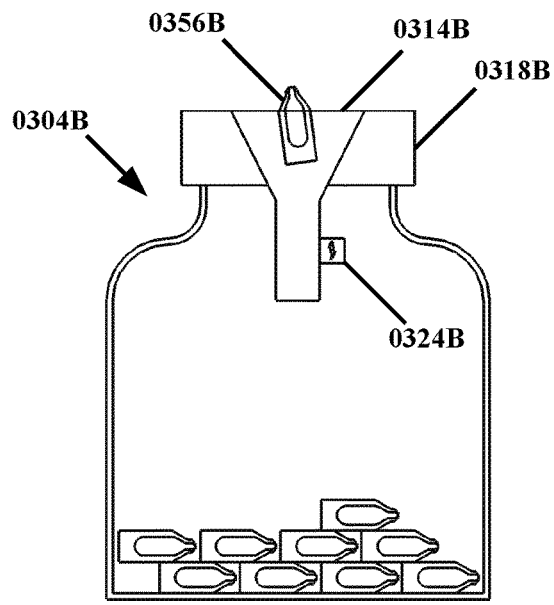
FIG. 3A  FIG. 3B
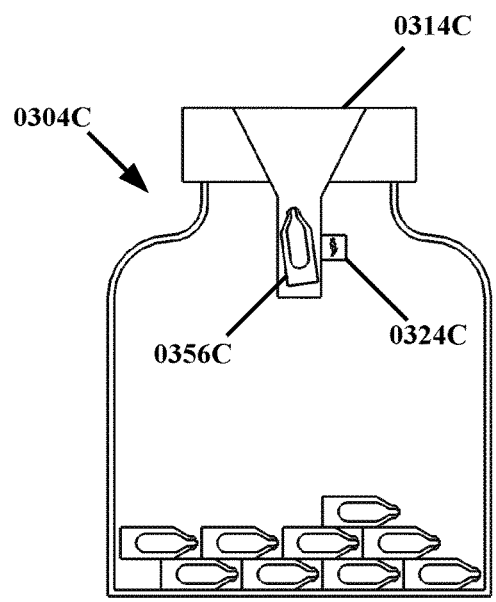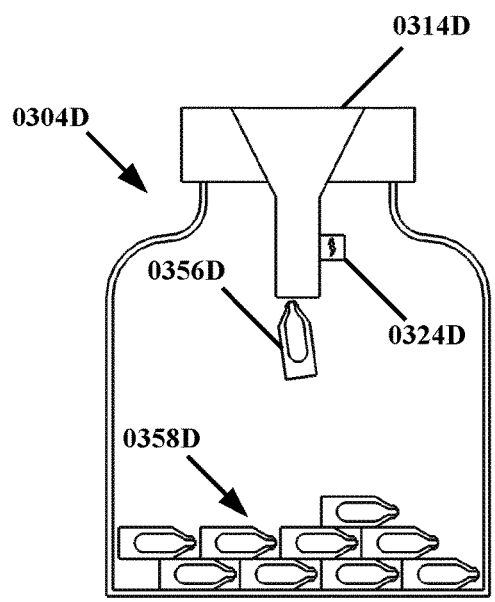
FIG. 3C  FIG. 3D

METHOD AND APPARATUS FOR SMART MEDICATION AUTHENTICATION THROUGH CONSIDERING NON-SMART INCIDENTAL MATERIALS

CROSS-REFERENCE TO RELATED APPLICATIONS

This application claims priority to U.S. Provisional Application Ser. No. 62/614,194 filed Jan. 5, 2018, which is incorporated herein by reference for all purposes.

FIELD OF THE INVENTION

Various embodiments concern acquiring information indicative of the use of medication. More particularly, various embodiments relate to providing a positive indication that medication is being taken, dispensed, prepared for use, etc., in a manner that does not require directed signaling action on the part of the user or an active (e.g., electrically powered) system for signaling, and that does not require network connectivity (i.e., "smart" functionality) in/on the medication container itself.

BACKGROUND

Typically, a medication may be dispensed with a regimen according to which a patient is to use that medication. The regimen may be a prescription for treating a patient, instructions for conducting a clinical study, directions for an over-the-counter medication, etc. Certain medications may lose effectiveness, present side effects, etc., if not taken according to the indicated regimen. Also, non-adherence to a regimen may affect clinical study data regarding the effectiveness, safety, etc. of a medication, to a degree that may be unknown and at least potentially significant. (Similarly, certain products other than medications may be dispensed with regimens or analogs thereto.)

Using patient self-reporting to determine adherence may present difficulties if patients do not reliably record the use of the medication; again, the degree of non-adherence may not be known. Use of network-connected systems (also referred to as "smart" systems) to generate authenticated data (e.g., taken automatically by sensors) may avoid some self-reporting issues, but may present other issues. For example, a "smart" medication container with on-board sensors, processor, etc. may be expensive, delicate, environmentally unfriendly, etc. This may be particularly true for medication containers that are used once or a few times and then discarded, such as single-use vials or ampoules of eyedrop medication, single-dose blister packs of pills, single-use hypodermic syringes, etc.

Furthermore, for certain arrangements the actual use of medication may approximate an "instant" event, e.g., it may take a very short time to carry out the specific act of swallowing a pill, instilling an eyedrop, injecting insulin, etc. In such case, tracking the use of the medication in itself may rely upon a relatively brief window of time for detection. If determining medication use requires detecting medication use in real time, e.g., during the actual event of dispensing or swallowing the pill, etc., then even relatively brief interruptions in system function may compromise monitoring. Considering a battery-operated sensor engaged with a pill bottle as an example, if the battery dies then any medication events that take place during the time the battery was dead may go undetected. Similarly, a system that relies on communicating a wireless signal at the time medication is taken may nominally detect the use of medication but still fail to register that use if wireless communication is inoperative for some reason (lack of signal, interference, etc.). As another example, if a patient forgets to carry or deliberately does not carry a medication monitoring device with them for some period of time, then doses of medication taken during that period may not be detected or otherwise registered.

This disclosure presents certain examples and explanations for the purpose of illustration. These examples and explanations should not be construed as exhaustive or limiting.

BRIEF SUMMARY OF THE INVENTION

This disclosure contemplates a variety of systems, apparatus, methods, and paradigms for targeted and/or interactive approaches for determining the use of medication or other products through consideration of incidental materials associated therewith.

In one embodiment a method is provided, including instantiating a regimen standard for a medication regimen on a processor engaged with a bin, and instantiating a container sensing standard on the processor. The method includes receiving a used single-dose medication container in the bin, via a chute of the bin, and generating first, second, and third sensor signals from respective first, second, and third light-beam sensors engaged with the chute, the sensors being configured such that light beams thereof are interrupted sequentially by the container in passing through the chute. The method includes communicating the sensor signals to the processor, and then determining in the processor a container correspondence state of the sensor signals with the container sensing standard.

The method includes, in response to determining a positive container correspondence state, registering a medication container disposal event and an event time therefor with the processor, including recording the event and the event time in a data store of the bin, communicating the event and the event time to an external entity via a wireless communicator of the bin, and presenting the event and the event time via a graphical display of the bin. The method also includes determining an adherence correspondence state of the event and the event time to the regimen standard in the processor, and registering the adherence correspondence state, including recording the adherence correspondence state in the data store, communicating the adherence correspondence state to the external entity, and presenting the adherence correspondence state via the display.

In another embodiment a method is provided that includes receiving an incidental material associated with a medication in a bin, detecting with a sensor the incidental material in the bin, and generating a sensor signal indicative thereof, and communicating the sensor signal to a processor. The method includes identifying the sensor signal as being consistent with the incidental material in the bin in the processor, and in response to identifying the sensor signal as consistent, registering in the processor a contextual event and a contextual event time. The method also includes determining from the contextual event and contextual event time an adherence to a regimen for the medication.

The incidental material may include a container for the medication, packaging for the medication, a delivery implement for the medication, an unused portion of the medication, and/or a marker for the medication. The incidental material may include at least a portion of a single-use eye drop vial.

Receiving the incidental material may include the incidental material passing through a bin lid of the bin into a bin body of the bin. Detecting the incidental material in the bin may include detecting an entry of the incidental material into the bin. Detecting the incidental material in the bin may include detecting a passage of the incidental material through the bin lid into the bin body. Detecting the incidental material in the bin may include optically detecting a presence of the incidental material within the bin lid. Detecting the incidental material in the bin may include optically detecting a motion of the incidental material through the bin lid. Detecting the incidental material may include at least one of light beam detection, optical image detection, capacitive detection, inductive detection, ultrasonic motion detection, impact detection, weight detection, and acoustic detection. Detecting the incidental material in the bin may include a plurality of sensors and generating a plurality of sensor signals indicative thereof.

The processor may include a cloud processor. The method may include communicating the contextual event and contextual time to an entity external to the bin, and then determining the adherence externally from the bin. The method may include determining the adherence in a cloud processor.

In another embodiment an apparatus is provided that includes a bin adapted to receive therein an incidental material associated with a medication, at least one sensor adapted to sense the incidental material in the bin and to generate a sensor signal indicative thereof, and a processor in communication with the sensor. The processor is adapted to identify the sensor signal as being consistent with the incidental material in the bin, register a contextual event and a contextual event time in response to identifying the sensor signal, and determine from the contextual event and contextual event time an adherence to a regimen for the medication.

The bin may include a bin body and a bin lid removably engaged with the bin body. The bin body may be adapted to accumulate the incidental material therein. The bin lid may be adapted to pass the incidental material therethrough to the bin body. The sensor and the processor may be engaged with the bin lid so as to be removable therewith from the bin body.

In another embodiment an apparatus is provided that includes a bin lid adapted to removably engage with a bin body and adapted to pass an incidental material associated with a medication therethrough to the bin body, at least one sensor adapted to sense the incidental material in the bin and to generate a sensor signal indicative thereof, the sensor being engaged with the bin lid, and a processor in communication with the sensor and engaged with the bin lid. The processor is adapted to, identify the sensor signal as being consistent with the incidental material in the bin body, register a contextual event and a contextual event time in response to identifying the sensor signal, and determine from the contextual event and contextual event time an adherence to a regimen for the medication.

The bin lid may define an aperture therethrough, the sensor being in communication therewith so as to sense the incidental material therein. The sensor may be adapted to sense the incidental material without active signaling by the incidental material. The sensor may be adapted to sense the incidental material without sensor targets on the incidental material. The sensor may include at least one of a light beam sensor, an optical imager, a capacitance sensor, an inductive sensor, an ultrasonic sensor, an impact sensor, a weight sensor, and an acoustic sensor. The apparatus may include a plurality of sensors.

The apparatus may include first, second, and third light beam sensors in communication with the aperture, the first, second, and third light beam sensors being disposed at first, second, and third orientations with respect to the aperture and at first, second, and third depths of the aperture.

In another embodiment an apparatus is provided that includes means for receiving an incidental material associated with a medication and means for detecting the incidental material in the bin and generating a signal indicative thereof. The apparatus also includes means for identifying the signal as being consistent with the incidental material, means for registering a contextual event and a contextual event time in response to identifying the signal, and means for determining from the contextual event and contextual event time an adherence to a regimen for the medication.

BRIEF DESCRIPTION OF THE SEVERAL VIEWS OF THE DRAWINGS

Various objects, features, and characteristics will become more apparent to those skilled in the art from a study of the following Detailed Description in conjunction with the appended claims and drawings, all of which form a part of this specification. While the accompanying drawings include illustrations of various embodiments, the drawings are not intended to limit the claimed subject matter.

FIG. 3A through FIG. 3D show an example of medication containers being received within a bin, in cross-section.

Figure 1:
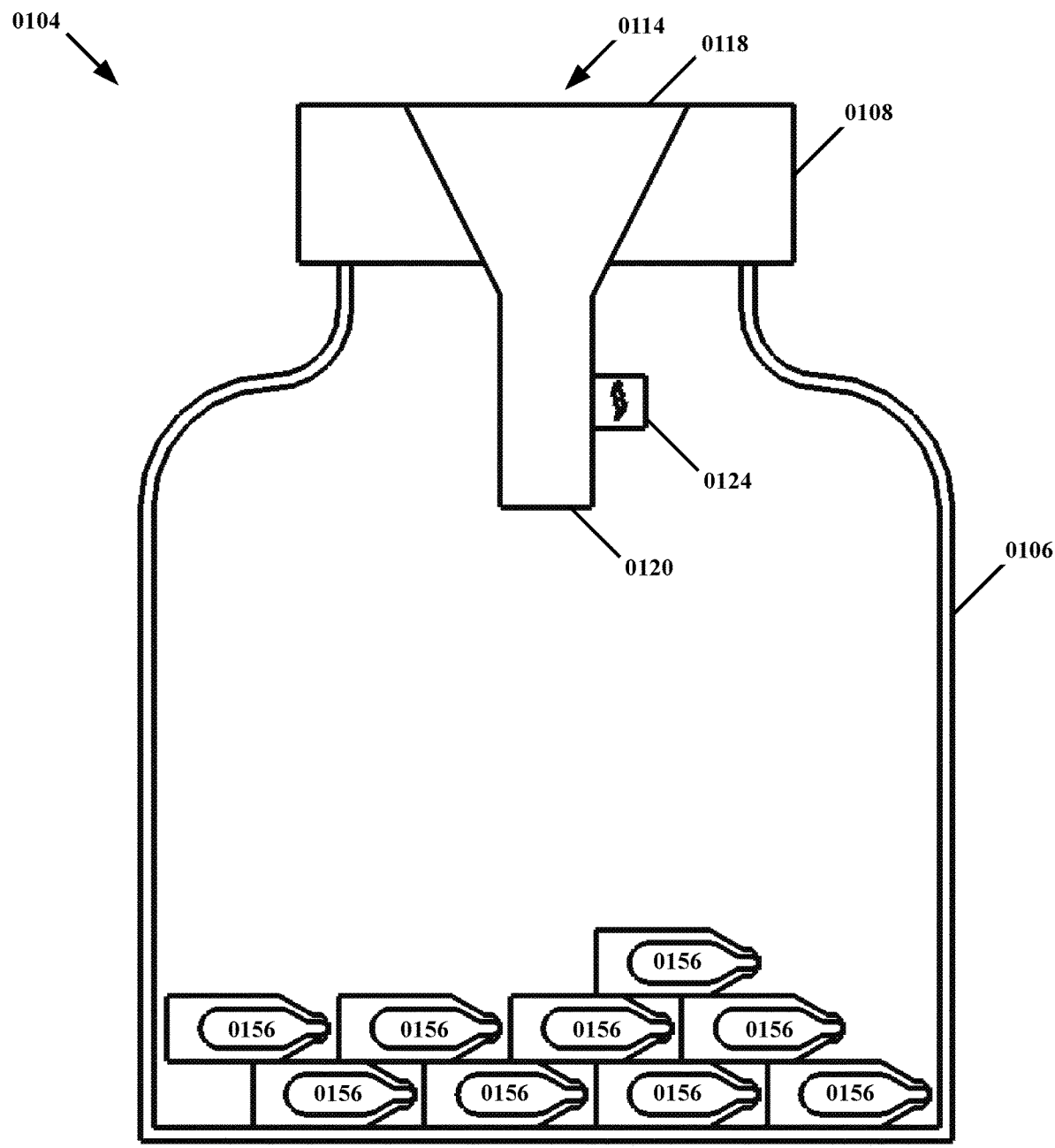
FIG. 1 shows an example bin for smart medication authentication through considering non-smart incidental materials, in cross-section.

The figures depict various embodiments described throughout the Detailed Description for the purposes of illustration only. While specific embodiments have been shown by way of example in the drawings and are described in detail below, the technology is amenable to various modifications and alternative forms. The intention is not to limit the technology to the particular embodiments described. Accordingly, the claimed subject matter is intended to cover all modifications, equivalents, and alternatives falling within the scope of the technology as defined by the appended claims.

DETAILED DESCRIPTION OF THE INVENTION

Various embodiments are described herein that relate to determining/authenticating the use of a medication or other product/service through consideration of incidental materials therefrom.

Certain medications may be provided in containers holding a single dose or a few doses. Examples include but are not limited to single-use eye drop vials, blister packs holding individual pills, hypodermic syringes and auto-injectors holding medications such as insulin or epinephrine, dermal patches, single-use tubes of ointment, etc. Particularly in such cases, material related but incidental to the medication itself may remain once the medication is administered, such as empty vials and blister packs, etc. While the presence of such incidental material in itself may not document the actual use of medication with absolute certainty, incidental material may provide context from which it may be inferred that medication likely was taken. For example, an empty single-use vial may be strong evidence (if not necessarily incontrovertible proof) that the medication originally in that vial was used. Thus, identifying incidental material associated with medication may facilitate determinations of whether a medication was used, and possibly other information such as when, how, in what dose, etc.

If a receptacle is provided with suitable smart capabilities, smart functionality may be achieved even if the medication containers themselves are "dumb." As a more concrete example, if jar or bin is equipped with sensors adapted to identify when empty single-use eye drop vials are deposited therein, the use and time of use of the eye drops may be determined at least approximately. The vials themselves may not be required to have any smart systems or functionality (or other unusual properties), so long as the sensors are suitable to detect the empty vials being dropped into the bin. Although the individual vials themselves may be single-use, a suitable bin may accommodate many such vials, registering each one as deposited therein. The bin also may be reusable, e.g., the bin may be emptied from time to time and used indefinitely. Thus, the burden of providing suitable sensors, processors, etc., may be reduced compared to an arrangement wherein each medication container, delivery device, or medication itself (e.g., a smart pill) incorporates smart hardware. For example, rather than equipping a disposable single-use container with sensors and/or other smart components, with the expectation that those components may be discarded after a single use along with the container, smart components engaged with a bin may operate for many doses of medication dispensed over considerable periods of time. Reusing rather than discarding components may reduce costs, reduce material consumption, reduce issues regarding disposal of electronic components on expended containers, etc.

Thus, by "offloading" smart components from the containers to a bin wherein containers or parts thereof may be disposed of, smart functionality may be enabled for authenticating that medication is being used according to some regimen, while the medication containers and/or other incidental materials themselves are "dumb." In authenticating the use of medication and/or other products and/or services, determinations of adherence to a regimen may be improved (e.g., as compared with self-reporting), adherence to that regimen itself may be improved, and/or outcomes with regard to patient treatment, clinical trials, etc. may be improved.

FIG. 1 shows an example arrangement of a bin 0104 adapted to receive therein used medication containers 0156 (as an example of material incidental to medication use, thus potentially providing evidence of at least the context of medication use). As illustrated the bin 0104 is a jar having a body 0106 and a lid 0108, and the used medication containers 0156 already therein are empty single-use vials as may be used to dispense eye drops. The bin lid 0108 has a chute 0114 defining an aperture therethrough with openings at a mouth 0118 and a tail 0120 thereof, the chute 0114 being approximately conical in an upper portion extending from the mouth 0118 and straight in a lower portion extending to the tail 0120. A sensor 0124 is engaged with the lower portion of the chute 0114.

Figure 2A:
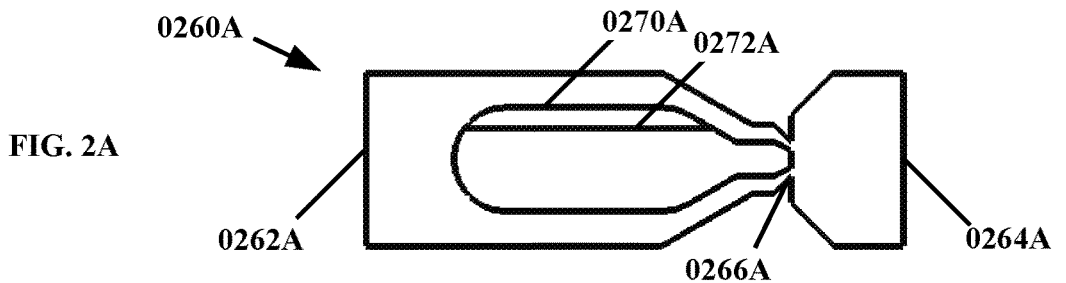
FIG. 2A though FIG. 2E show example single-use medication containers in various states of use, in cross-section.

FIG. 2A through FIG. 2E. show several examples of single-use vials as may be comparable to those in FIG. 1 and certain other illustrations herein. FIG. 2A shows an unused single-use vial 0260A with a liquid medication 0272A therein. The vial 0260A has a body 0262A defining a cavity 0270A therein, adapted to contain the medication 0272A, and a cap 0264A, the cap 0264A obstructing the medication 0272A from exiting in the configuration shown. The vial 0260A exhibits notches 0266A so as to be frangible at a point between the body 0262A and the cap 0264A. Thus, the vial 0260A may be considered as a single piece prior to use (e.g., an integrally-molded plastic component).

Figure 2B:
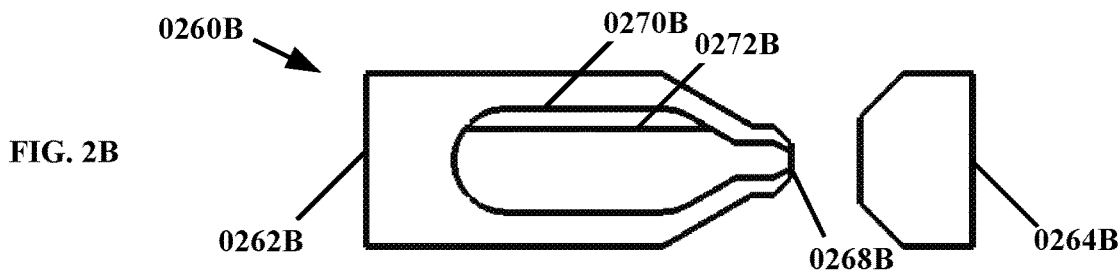

As shown in FIG. 2B, for use the vial 0260B may be opened by separating the cap 0264B from the body 0262B. In such configuration the vial 0260B is open. With the cap 0264B removed, a spout 0268B is exposed such that medication 0272B may exit the cavity 0270B via the spout 0268B. The cap 0264B typically may not be replaceable, and/or may not be replaced even if replaceable (though replaceable caps and replacing caps are not prohibited). In the arrangement shown in FIG. 2B, the cap 0264B is permanently separated from the body 0262B by breaking/tearing the vial 0260B at the former notches thereof. In other embodiments, the cap 0264B may be detachably connectable to the body 0262B (e.g., via a threaded fastener or another mechanical feature). Moreover, the cap 0264B may not necessarily be removed from the body 0262B in its entirety. For example, the cap 0264B may remain fixed to the body 0262B along one side so as to remain connected to the body 0262B but allow fluid flow through the spout 0268B.

Figure 2C:
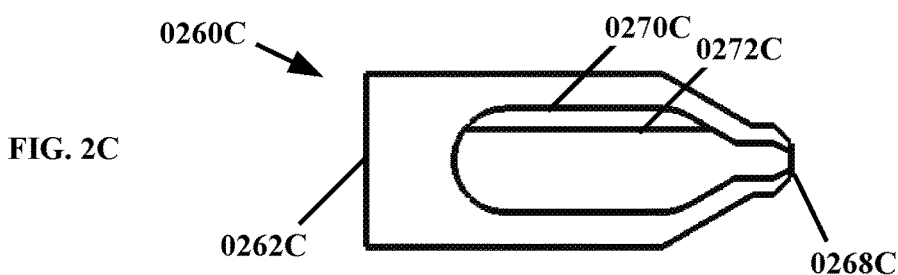
Figure 2D:
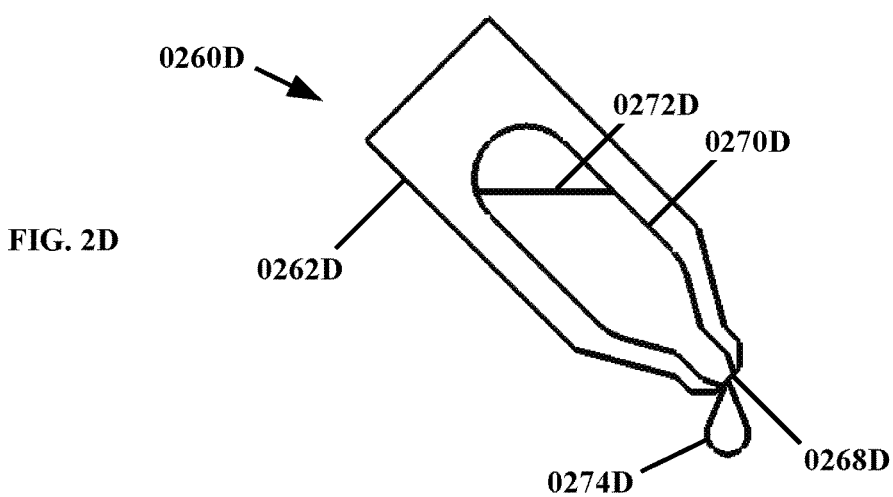

As is shown in FIG. 2C, the cap may be discarded, so that only the body 0262C of the vial 0260C is considered after opening. For example, in dispensing medication 0272C from the cavity 0270C via the spout 0268C, in at least certain embodiments the cap 0264C may be ignored. Turning to FIG. 2D, once the vial 0260D is open as shown therein medication 0272D within the cavity 0270D may be dispensed via the spout 0268D, for example in a dispersal 0274D shown in the form of a droplet of liquid medication. The dispersal 0274D may be created, for example, responsive to an application of pressure along the exterior surface of the body 0262D.

Figure 2E:
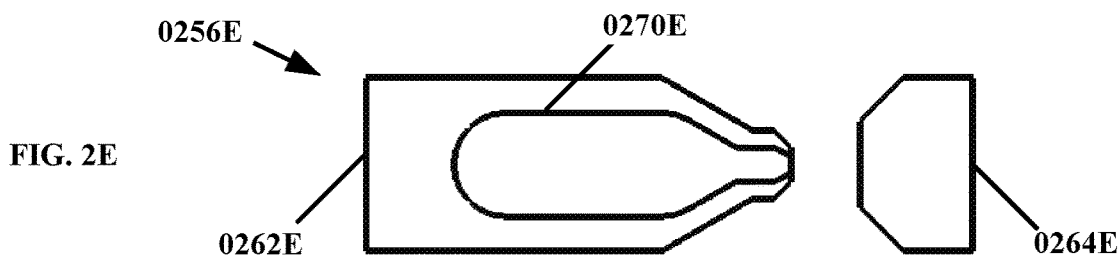

Once the medication has been used, the used vial 0256E and the cap 0264E may remain behind; one or both of the body 0262E and cap 0264E may be considered as incidental material for the use of the medication. It is noted that although a vial is referred to as being a "used vial" 0256E, and may in certain instances herein be referred to as being empty, expended, etc., it is not necessarily required that the cavity 0270E thereof be completely empty of medication (although for illustrative purposes the used vial 0256E is shown in FIG. 2E as being completely empty). For example, some medication may be left in a used vial 0256E by oversight, because the cavity 0270E could not be fully emptied, or even by design (e.g., a single use eye drop container may hold slightly more than the prescribed dose, on the expectation that users may at times blink, miss their eye, or otherwise fail to properly instill a dispersal). Indeed, as noted elsewhere herein in certain embodiments it may be useful to detect and/or measure remaining medication. However, for simplicity it may be suitable in at least some cases to consider used vials 0256E as empty even if some residual medication may remain therein.

FIG. 3A through FIG. 3D collectively show operation of an example bin, as may be similar to that already shown in FIG. 1. In FIG. 3A, a bin 0304A is shown with a lid 0318A, chute 0314A, and a sensor 0324A. An accumulation 0358A of used single-use vials (not individually numbered) is shown within the bin 0304A. In the configuration illustrated the bin 0304A may be considered as inactive (though ongoing operation of certain functions is not prohibited).

Turning to FIG. 3B, at some point a single-use vial may be used to dispense medication; the actual use of the medication may not be identified per se, and is not explicitly shown. However, in FIG. 3B an empty single-use vial 0356B is shown, being received into the chute 0314B of the lid 0318B of the bin 0304B (though the used vial 0356B has not yet approached the sensor 0324B as shown). Given that a used vial 0356B as formerly contained medication is being disposed of in the bin 0304B, it may be inferred with at least some confidence that the medication formerly in that vial 0356B has been dispensed and/or administered.

As may be seen with regard to the bin 0304C shown in FIG. 3C, in passing through the chute 0314C the used vial 0356C comes into proximity with the sensor 0324C engaged with the chute 0314C. The sensor 0324C may generate a sensor signal consistent with the passage of such a vial 0356C through the chute 0314C; such a sensor signal then may be communicated to a processor (not shown; in practice a processor may be engaged with the bin 0304C, but this is not required) for evaluation.

Continuing in FIG. 3D, the used vial 0356D then exits the chute 0314D and moves out of proximity with the sensor 0324D, falling within the bin 0304D so as to eventually join the accumulation 0358D of incidental material on the floor of the bin (though impact and rest of the used vial 0356D are not explicitly shown in FIG. 3D).

Given arrangements such as are shown in FIG. 3A through FIG. 3D, for a sensor signal communicated to a processor the processor may identify the sensor signal as being consistent (or not) with the anticipated incidental material for a medication. The nature of such identification may depend on the particulars of the incidental material(s), the sensor(s), etc. For example, a capacitance sensor may detect changes in capacitance within the chute, e.g., between two or more conductive pads, as the vial passes therebetween, while a photo sensor may detect changes in transmitted and/or reflected light within the chute. Typically, though not necessarily, some definition may be provided as to what sensor signal is to be expected as representing a vial being received within the bin, as opposed to a false positive, data error, etc. Such definitions may be numerical (e.g., a range of values as measured by the sensor), graphical (some shape to a curve of measured value over time, etc.), or other forms without limit. Likewise, the simplicity or complexity of such a definition also is not limited.

If the sensor signal is identified as being consistent with incidental material being present and/or entering the bin, the processor may register a contextual event and a contextual event time. The term "contextual event" refers to the nature of what is being detected. It may be inferred that medication has been used if an empty medication is identified; however, the event that is actually detected via sensors in such instance typically is not the use of the medication per se, but the disposal/storage/etc. of the empty container that formerly held that medication. Thus, for certain embodiments it may be useful to distinguish the events being detected as events contextual to the use of medication, but not medication events themselves. For example, such distinction may be useful in subsequent data processing, e.g., information may be identified based on when a patient disposes of the empty container, that may not be entirely equivalent (though not necessarily inferior) to information explicitly on when the patient takes the medication. However, other embodiments may not make such a distinction; it may be suitable in some instances to consider the contextual event of disposing of incidental material and a medication event as being interchangeable.

The form of registration also is not limited. Registration may include, but is not limited to, generating an event flag or other data object within a processor, recording data on a data store, communicating data to an external recipient, etc. So long as the event in question (e.g., discarding an empty medication vial) is in some manner noted, the manner of noting that event and other details of registration (such as what other information besides the event itself) is not limited.

The processor also may determine a contextual event time. Typically, though not necessarily this may be the time (e.g., as determined by a chronometer on-board the processor) that the sensor signal indicated the presence of the incidental material. Other information also may be determined. For example, certain sensors may provide information regarding how much medication (if any) remains in the empty vial, based on the capacitance, the optical transmission, an image captured, etc. The information that may be determined from the sensor signal and/or other sources is not limited.

Furthermore, the processor may consider the contextual event and/or the time thereof in making a determination as to whether a medication regimen for a medication under consideration is being adhered to. That is, is the patient taking the medication as directed? This may be determined for example based on whether empty vials (or other incidental materials) are received, at what times, in what numbers, with how much medication remaining, etc. Typically, though not necessarily such determinations may be made using multiple contextual events. For example, to know whether a patient is taking medication reliably according to a specified regimen, it may be necessary to collect data over several days, weeks, etc. However, single-event determinations—e.g., "was the medication taken today promptly at 9:15 AM as specified"—also may be suitable.

The form and location of the processor is not limited. A digital chip may for example be disposed on the lid or body of a bin. However, a processor external to the bin also may be suitable if the sensor signal is communicated thereto, e.g., through wireless communication. In such manner a separate processor such as that in a smart phone or other device may evaluate the sensor signal. Furthermore, the processor may not be a well-defined physical entity at all; some or all processor functions may be carried out through cloud computing, for example. Other arrangements also may be suitable, and embodiments are not limited with regard to the processor.

Similarly, the form, nature, and operation of the sensor is not limited. For certain embodiments it may be useful to dispose one or more sensors on or near the chute or some other aperture into the bin, if the incidental material is anticipated to enter through that aperture. However, it may also be suitable to dispose sensors elsewhere. For example, an imager may be disposed at many locations in a bin (or even externally) to obtain images showing how many empty vials are present, new empty vials being added, etc. Suitable sensors may include but are not limited to light beam sensors, optical imagers, capacitance sensors, inductive sensors, ultrasonic sensors, impact sensors, weight sensors, and acoustic sensors.

Multiple sensors may be present. The use of multiple sensors, even of the same type and in close proximity, may provide additional useful information.

An example arrangement utilizing multiple sensors is shown in FIG. 4A through FIG. 4H. In FIG. 4A through FIG. 4H a bin at least somewhat similar to that in FIG. 1 is shown, but with three sensors engaged with the chute rather than one. As shown, the first, second, and third sensors are light beam sensors, as may function by producing light beams (as indicated by the dashed arrows pointing to the left) in an emitter portion and detecting that light beam in a detector portion. Thus, though each sensor shown in FIG. 4A through FIG. 4H in two sections, each pair of sections is considered herein as a single sensor (though considering the sections separately would not be prohibited).

Figure 4A:
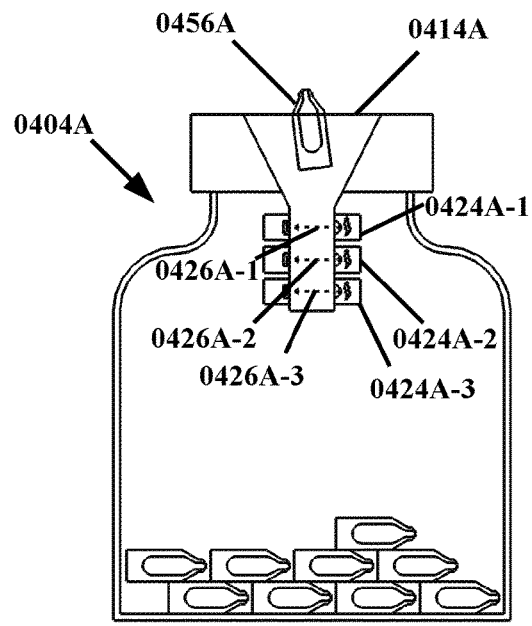
FIG. 4A through FIG. 4H show an example of a medication container being received within a bin having multiple sensors, in cross-section.

Specifically in FIG. 4A, a used vial 0456A is shown entering the chute 0414A of a bin 0404A, for example as if deposited by a patient who has dispensed medication from that vial used vial 0456A. As may be seen, three sensors 0424A-1, 0424A-2, 0424A-3 are disposed along the chute 0414A, illustrated for explanatory purposes as being photobeam sensors with light beams 0426A-1, 0426A-2, 0426A-3. In the configuration shown in FIG. 4A, the used vial 0456A has not interrupted any of the light beams 0426A-1, 0426A-2, 0426A-3 of the sensors 0424A-1, 0424A-2, 0424A-3.

Figure 4B:
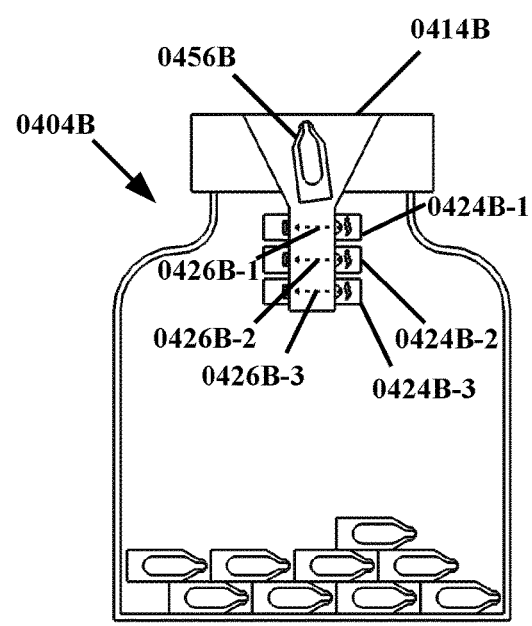

Continuing in FIG. 4B, the used vial 0456B has proceeded down the chute 0414B (e.g., under the force of gravity, though active motion systems, mechanical feeds, etc., are not prohibited) within the bin 0404B, but still has not interrupted any light beams 0426B-1, 0426B-2, 0426B-3 of the sensors 0424B-1, 0424B-2, 0424B-3.

Figure 4C:
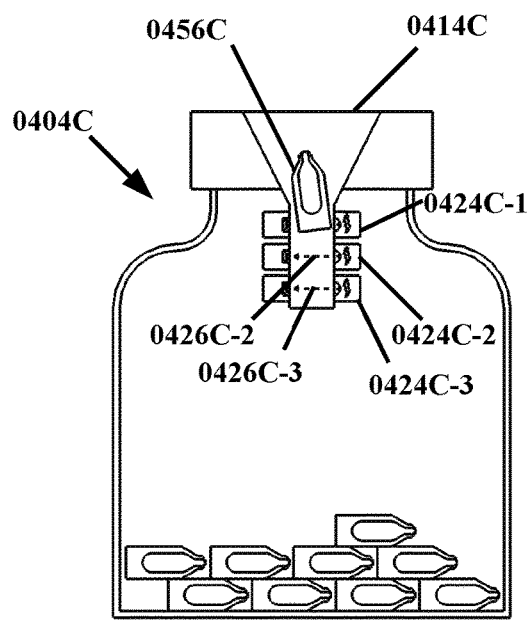

In FIG. 4C, the empty vial 0456C has moved down the chute 0414C within the bin 0404C far enough to interrupt a first light beam of the first sensor 0424C-1 from passing between the emitter and the detector thereof. (The interrupted first light beam is no longer shown explicitly in FIG. 4C, for clarity.) Consequently, the first sensor 0424C-1 may register the lack of detected light (or a reduction or other change in detected light), as may for example represent the presence of an object within the chute 0414C proximate the first sensor 0424C-1. However, light beams 0426C-2 and 0426C-3 for sensors 0424C-2 and 0424C-3 remain unobstructed in FIG. 4C.

Figure 4D:
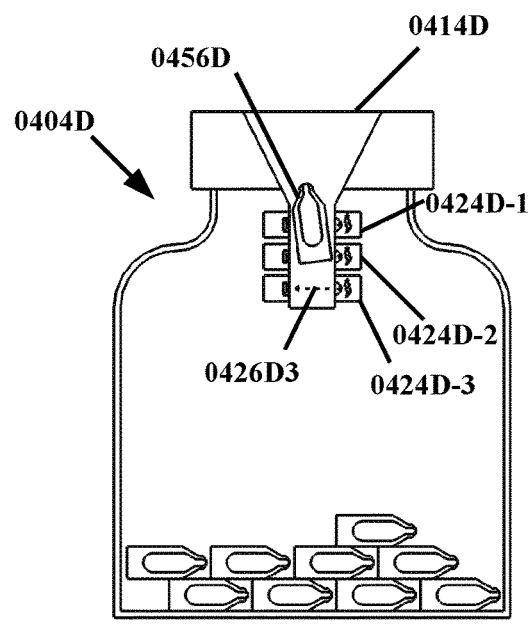
Figure 4E:
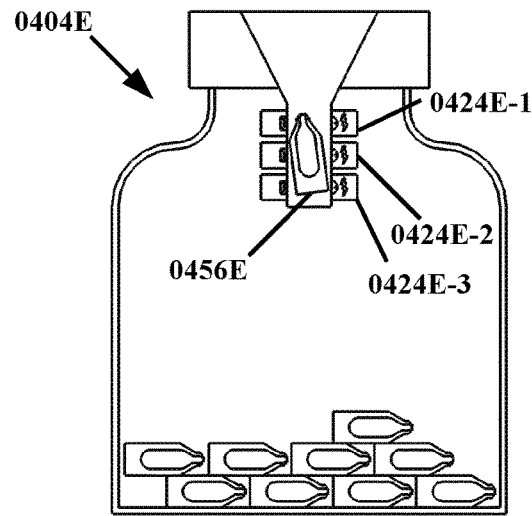

Moving on to the bin 0404D shown in FIG. 4D, the vial 0456D has continued to move down the chute 0414D within the bin 0404D and now interrupts light beams for the first and second sensors 0424D-1 and 0424D-2, so that the first and second sensors 0424D-1 and 0424D-2 may register a change in detected light (e.g., a decrease from the used vial 0456D obstructing light beams). The light beam 0426C for sensor 0424D-3 remains unobstructed in FIG. 4D. Continuing, in the example bin 0404E illustrated in FIG. 4E, the vial 0456E now interrupts light beams for all of the first, second, and third sensors 0424E-1, 0424E-2, 0424E-3.

Figure 4F:
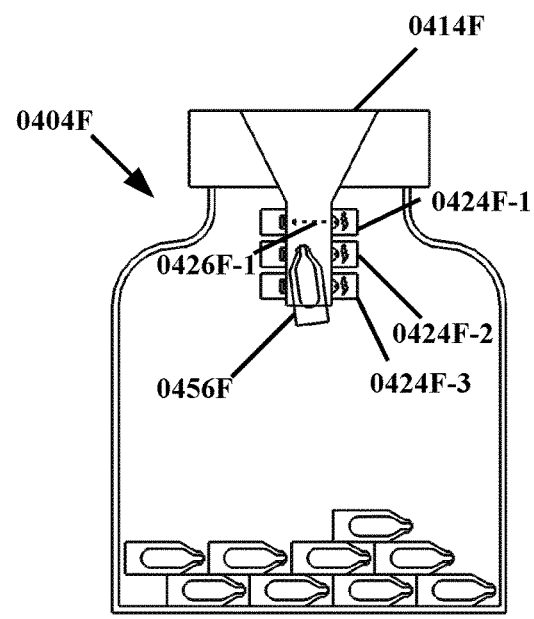
Figure 4G:
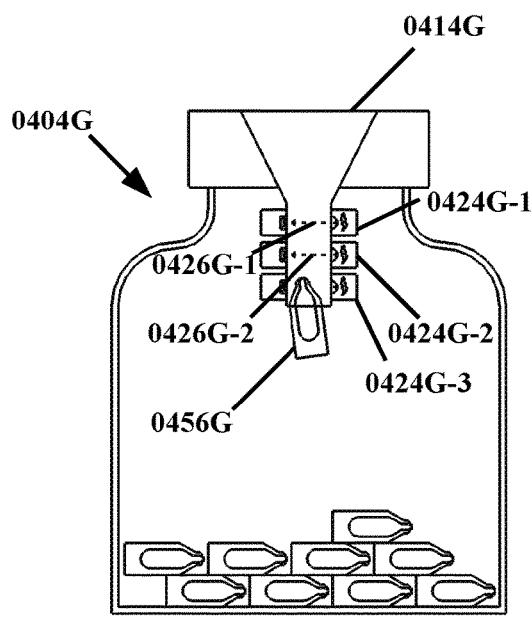
Figure 4H:
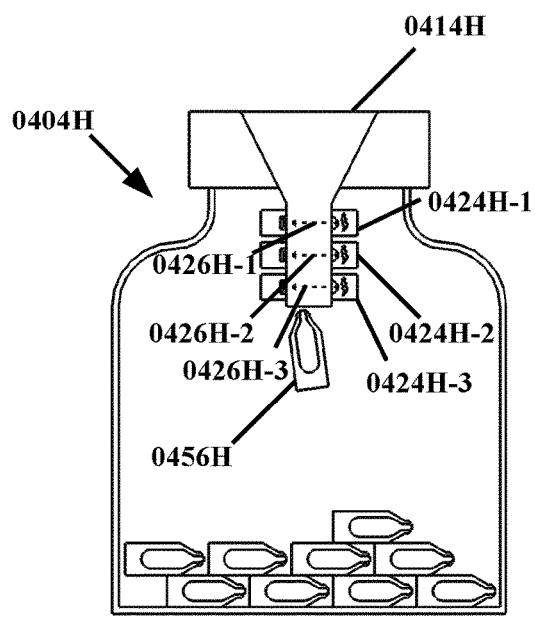

Continuing in FIG. 4F, the vial 0456F has moved far enough down the chute 0414F within the bin 0404F that the light beam 0426F-1 of the first sensor 0424F-1 is no longer interrupted thereby, although the vial still interrupts second and third light beams for the second and third sensors 0424F-2 and 0424F-3 respectively. Thus signals from the first sensor 0424F-1 may indicate that no object is presently proximate that sensor, though signals from the second and third sensors 0424F-2 and 0424F-3 may still indicate that an object is presently proximate thereto. In the bin 0404G as shown in FIG. 4G, the vial 0456G has descended through the chute 0414G so as to interrupt only a third light beam for the third sensor 0424G-3, with light beams 0426G-1 and 0426G-2 for the first and second sensors 0424G-1 and 0424G-2 unobstructed. In FIG. 4H, the vial 0456H has descended within the bin 0404H to exit the chute 0414H, and no longer obstructs any the light beams 0426H-1, 0426H-2, 0426H-3 from any of the sensors 0424H-1, 0424H-2, 0424H-3.

The arrangements in FIG. 4A through FIG. 4G consider gravity feed as an example. However, while as noted above gravity feed may be suitable for certain embodiments, use of gravity feed is not limiting. In addition, it is not required that the passage of incidental material into a bin be smooth, uniform, etc. For example, a bin may include a chamber to "sequester" a vial (or other incidental material) before proceeding into the remainder of the bin. A vial entering the bin could first enter such a chamber, and then move on (or be caused to move on) when another vial is received (e.g., the first vial being forced out physically by the second vial). Such an arrangement may be useful, for example in facilitating sensor operation. An object that is stationary or approximately so, even for a brief time, may be more readily sensed with at least certain sensors than an object moving past those sensors at speed. For example, imaging a stationary object at an approximately known position may be a simpler task than imaging an object in unconstrained motion (e.g., falling) through a chute. As such, rendering a vial stationary (or constrained, slowed, or otherwise "an easier target") may enable the use of imagers that are simpler, smaller, less expensive, less sophisticated, etc. Other sensors likewise may benefit from sequestering incidental material.

Furthermore, data processing also may be simplified, since sensor data may be more clear, less ambiguous, more abundant (due to having more time to collect such data), etc.; thus having more/better data may reduce demands for processing capability, power use, heat dissipation, etc.

In addition, sequestering incidental material may facilitate collection of additional types of data. For example, with more time (as may be provided by rendering a target object stationary, etc.) detecting and/or measuring the amount of medication remaining in a single-use vial (if any) may be facilitated (though measuring medication remaining and/or other features for vials that are in motion is not excluded). Likewise, if a vial or other object has markings thereon, rendering the vial stationary may facilitate detecting/reading the markings. Such markings may include lot numbers, dates of manufacture, expiration dates, bar codes, Quick Response (QR) codes, etc. It is noted that while it may not be necessary to provide purposed markings on incidental materials to serve as targets, the presence of such targets may be suitable and is not prohibited. Purposed markings may include but are not limited to printing of marks to facilitate optical detection, foil stamps to facilitate capacitive or inductive detection, etc. Likewise, the use of markings or other features as may already exist for other purposes (e.g., a label showing thereon the name of a medication, the dose, the prescribing physician, the patient, etc.) may be suitable.

Figure 5:
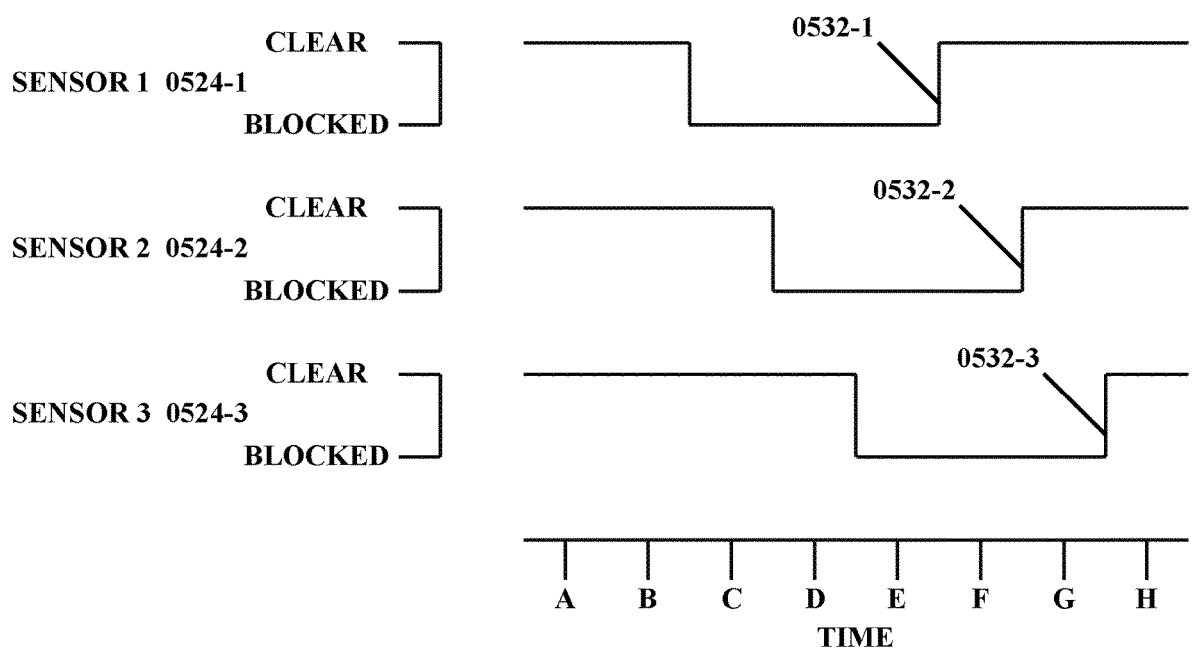
FIG. 5 shows example sensor signals for multiple sensors from a bin with a medication container being received therein, in plot view.

Moving on, FIG. 5 shows example sensor signals as may be produced by events similar to those shown in FIG. 4A through FIG. 4H. First, second, and third sensor signals 0532-1, 0532-2, 0532-3 are shown for three sensors, Sensor 1 0524-1, Sensor 2 0524-2, and Sensor 3 0524-3 (physical sensors are not shown, but for explanatory purposes it may be considered that such sensors may exist, and so are numbered distinctly in FIG. 5). The sensor signals 0532-1, 0532-2, 0532-3 as shown are binary, with states of either "clear" when no object is present proximate the respective sensors or "blocked" when an object is present. Such an arrangement may correspond with the use of light beam sensors such as shown in FIG. 4A through FIG. 4H. It is emphasized that the arrangement in FIG. 5 is an example only; other states, other types of data, etc., may be suitable, as may correspond with a wide range of sensors and sensor arrangements. In addition, even for light beam sensors, sensor signals therefrom are not limited only to binary arrangements; sensor signals may show variable light levels rather than simply "on/off," may indicate changes in transmitted, reflected, and/or absorbed light, may include changes in light color, direction, etc., and/or other factors.

However, considering as a simple example a binary state for sensors 0524-1, 0524-2, 0524-3, sensor signals 0532-1, 0532-2, 0532-3 as shown in FIG. 5 may be understood as representing passage of an empty vial through a bin as shown in FIG. 4A through FIG. 4H. For purposes of explanation, each time mark A through H (shown on a horizontal time axis in FIG. 5) may be considered as corresponding at least somewhat with arrangements shown in FIG. 4A through FIG. 4H, in sequence.

Thus at time A (e.g., as may correspond with an arrangement as in FIG. 4A) all three sensor signals 0532-1, 0532-2, 0532-3 from all three sensors 0524-1, 0524-2, 0524-3 show a signal of "clear." Likewise at time B all three sensor signals 0532-1, 0532-2, 0532-3 show "clear." At time C the first sensor signal 0532-1 reads "blocked," as may indicate an object interrupting a first light beam for the first sensor 0524-1, while the second and third sensor signals 0532-2 and 0532-3 still read "clear." At time D, the first and second sensor signals 0532-1, and 0532-2 read "blocked" while the third sensor signal 0532-3 reads "clear." At time E, all of the first, second, and third sensor signals 0532-1, 0532-2, 0532-3 report "blocked"; first, second, and third light beams for first, second, and third sensors 0524-1, 0524-2, 0524-3 all may be interrupted by an object such as an empty vial. At time F the first sensor signal 0532-A now returns "clear," while the second and third sensors 0532-2 and 0532-3 still read "blocked." At time G the first and second sensor signals 0532-1 and 0532-2 both read "clear," with the third sensor signal 0532-3 showing "blocked." Finally at time H all three sensors 0524-1, 0524-2, 0524-3 deliver sensor signals 0532-1, 0532-2, 0532-3 showing "clear."

Considering the various times and signals shown in FIG. 5 collectively, it may be understood that particular patterns of information in sensor signals may be exhibited for a vial (or other incidental material) passing through a chute (or otherwise being received in a bin), as may enable determination of features regarding that vial; the use of multiple sensors may facilitate emergence of such patterns, though use of single sensors is not excluded. Regardless, such informative patterns may be exhibited even if the sensor signals themselves are extremely simple, e.g., binary as shown in FIG. 5. Such patterns may enable determination of information sufficient to identify what is passing through the chute. For example, a vial of a given size moving past sensors in known positions may produce predictable patterns such as are shown in FIG. 5, e.g., blocking first one, then two, then all three light beams in sequence, and then clearing the first, second, and third sensors likewise in sequence. Such a pattern may be consistent with an object of a particular length, where objects of other dimensions may not show comparable patterns. Further, the use of multiple sensors may provide redundancy; if sensor 1 were to read "blocked," but neither sensor 2 nor sensor 3 subsequently reads blocked, then it may be inferred that some error or other mishap has occurred (since objects typically may not enter the bin and then be ejected without passing through). This may represent a sensor malfunction, someone putting a finger into the chute, etc. In such manner relatively complex conclusions—for example, that a specific object has entered and passed through a chute, or that sensors are malfunctioning—may be drawn from relatively simple data, such as binary readings for the obstruction of one or more sensors.

As a specific example of discrimination between a vial deposited in a bin and some other non-vial object (e.g., a cap) deposited therein, FIG. 6A through FIG. 6G, and FIG. 7 may be interpreted collectively as showing a cap entering a bin and sensor signals as may be produced therefrom. Comparison with FIG. 4A through FIG. 4H may illuminate certain functions, such as the aforementioned potential for discriminating among different incidental materials being received in a bin. Where FIG. 4A through FIG. 4H show an empty vial being received, FIG. 6A through FIG. 6G show a cap (as may have been removed from such a vial).

Figure 6A:
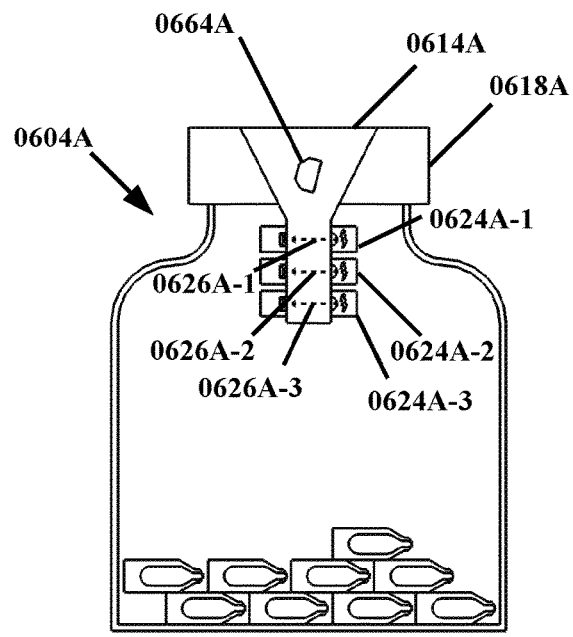
FIG. 6A through FIG. 6G show an example of a medication container cap being received within a bin having multiple sensors, in cross-section.
Figure 6B:
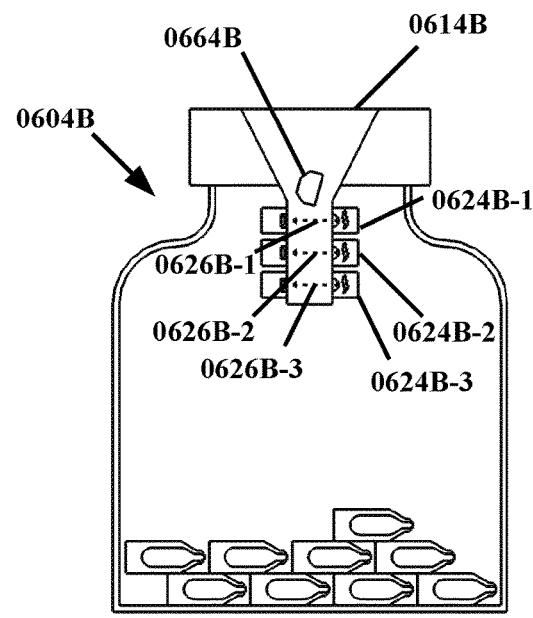
Figure 6C:
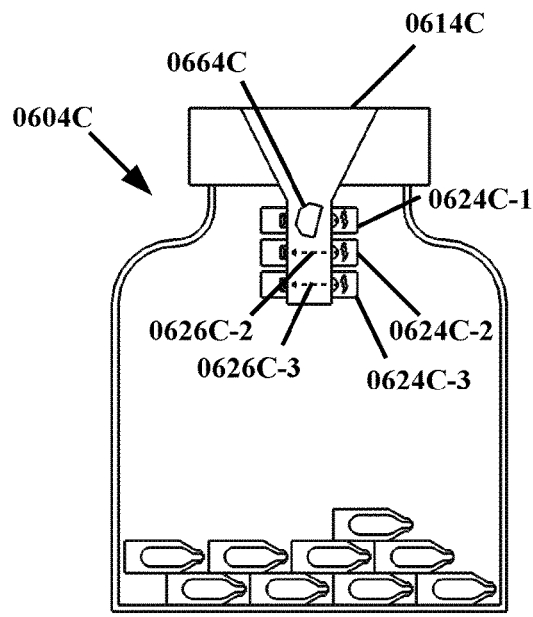
Figure 6D:
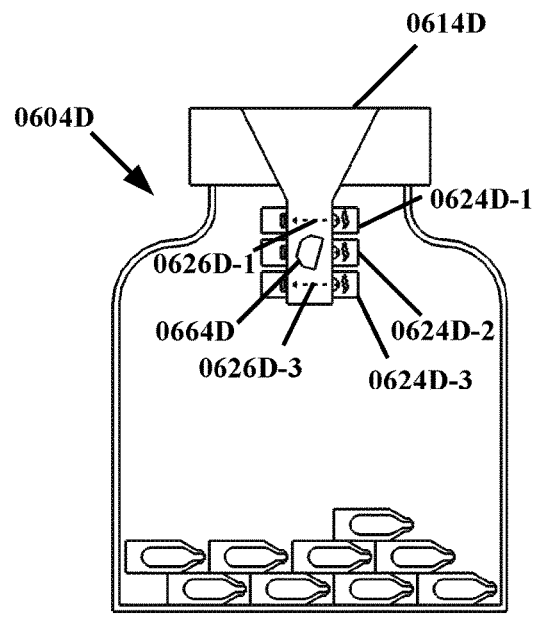

In FIG. 6A a cap 0664A from a used vial (not shown) enters a chute 0614A in the lid 0618A for a bin 0604A. None of first, second, and third light beams 0626A-1, 0626A-2, 0626A-3, from first, second and third sensors 0624A-1, 0624A-1, 0624A-1, are interrupted. Likewise in FIG. 6B the cap 0664B (while having moved downward) within the chute 0614B of the bin 0604B still does not interrupt first, second, and third light beams 0626B-1, 0626B-2, 0626B-3, from first, second and third sensors 0624B-1, 0624B-1, 0624B-1. However, in FIG. 6C, the cap 0664C has descended within the chute 0614C of the bin 0604C to interrupt a first light beam (interrupted beam not shown) for the first sensor 0624C-1; second and third light beams 0626C-2, 0626C-3 for second and third sensors 0624C-2, 0624C-3 are not interrupted. In FIG. 6D, the cap 0664D now is at a position within the chute 0614D of the bin 0604D as to interrupt second light beam of the second sensor 0624D-2, but no longer interrupts the first light beam 0626D-1 of the first sensor 0624D-1 and does not interrupt the third light beam 0626D-3 of the third sensor 0624D-3.

Figure 6E:
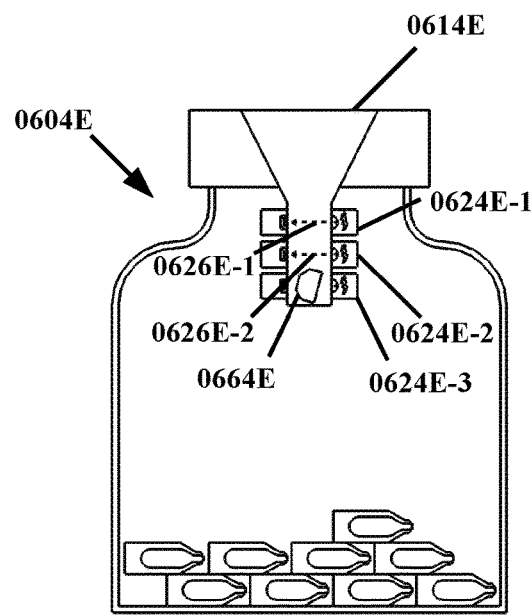
Figure 6F:
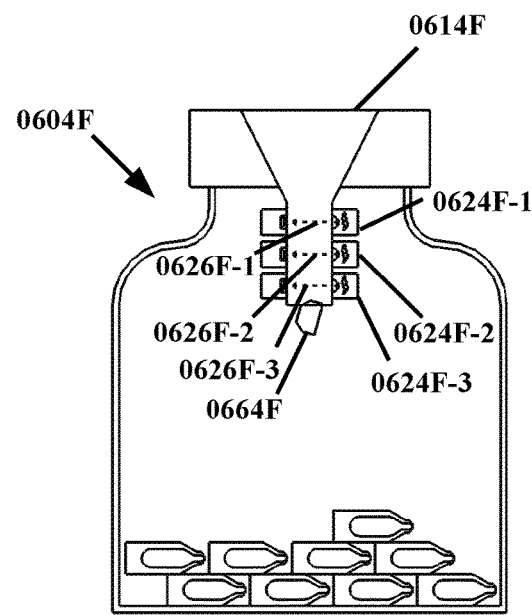
Figure 6G:
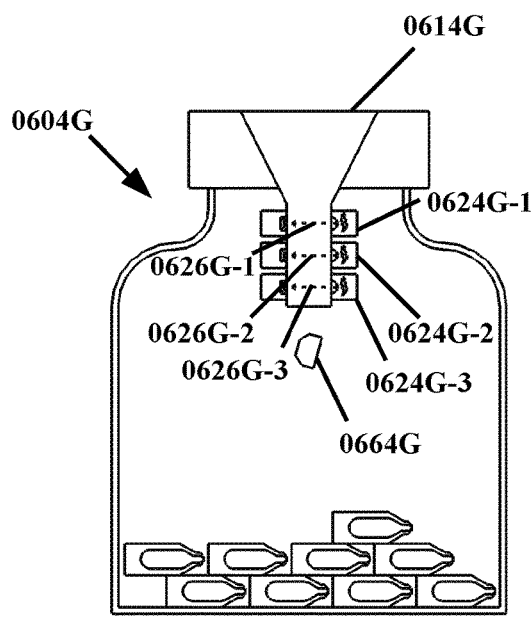

Continuing in FIG. 6E the cap 0664E has fallen through the chute 0614E in the bin 0604E so as to now interrupt a third light beam from a third sensor 0624E-3, but first and second light beams 0626E-1 and 0626E-2 from the first and second sensors 0624E-1 and 0624E-2 are not interrupted. In FIG. 6F the cap 0664F has descended in the chute 0614F within the bin 0604F so as to no longer interrupt any of the three light beams 0626F-1, 0626F-2, 0626F-3, from the first, second and third sensors 0624F-1, 0624F-2, 0624F-3. In FIG. 6G the cap 0664G is continuing to descend out of the chute 0614G of the bin 0604G, again not interrupting any of the light beams 0626G-1, 0626G-2, 0626G-3, from the first, second and third sensors 0624G-1, 0624G-1, 0624G-1.

Figure 7:
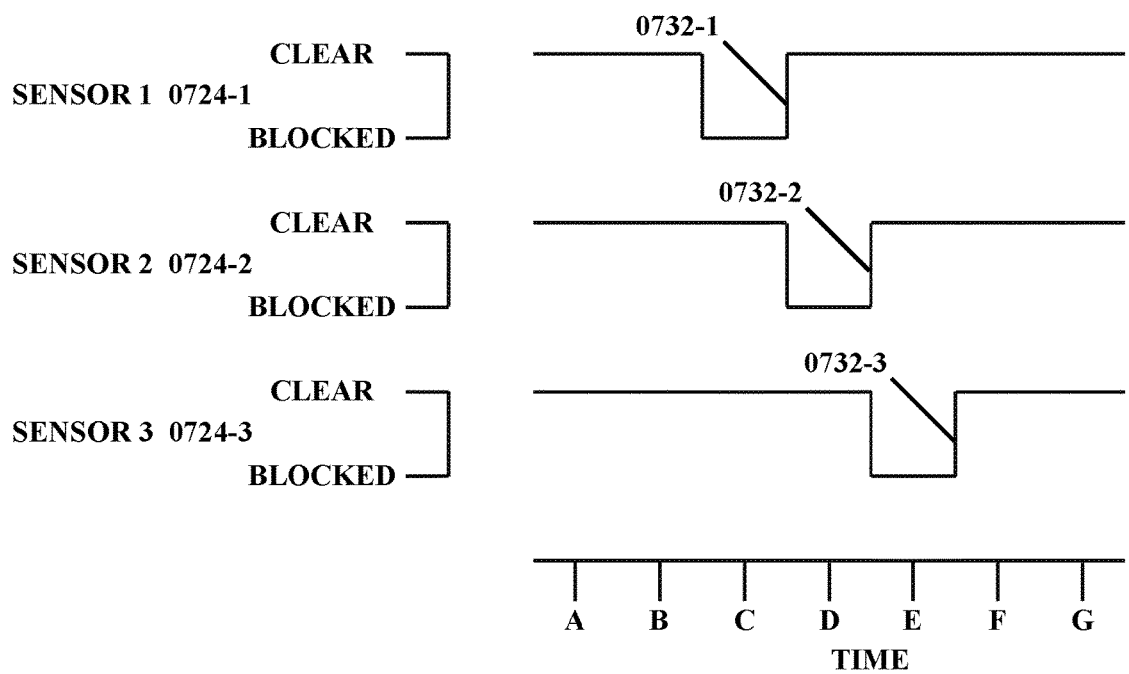
FIG. 7 shows example sensor signals for multiple sensors from a bin with a medication container cap being received therein, in plot view.

Turning now to FIG. 7, therein sensor signals are shown as may be produced by events similar to those shown in FIG. 6A through FIG. 6G. Sensor signals 0732-1, 0732-2, 0732-3, are shown for three sensors, Sensor 1 0724-1, Sensor 2 0724-1, and Sensor 3 0724-1, with states of "clear" or "blocked." The sensor signals 0732-1, 0732-2, 0732-3, as shown in FIG. 7 may represent passage of a vial cap through a bin chute. For purposes of explanation, each time A through G may be considered as corresponding with one of FIG. 6A through FIG. 6G in sequence. As may be seen, even though the bin, sensors, etc. as illustrated in FIG. 6A through FIG. 6G are similar to those in FIG. 4A through FIG. 4H, and an object is entering the bin, the sensor signals 0732-1, 0732-2, 0732-3 in FIG. 7 are not identical to those in FIG. 5.

One skilled in the art will recognize that additional information on the administration of medication could be gleaned by having separate bins for the bodies and caps of used vials. After administering medication from a vial, an individual may deposit the body of the vial in a first bin (e.g., as shown in FIG. 4A through FIG. 4H) and the cap of the vial in a second bin (e.g., as shown in FIG. 6A through FIG. 6G). By comparing the signal(s) generated by these bins, information such as the duration of medication administration may be estimated.

In FIG. 7 at time A (e.g., as may correspond with FIG. 6A) all three sensor signals 0732-1, 0732-2, 0732-3 are "clear." Likewise at time B all three sensor signals 0732-1, 0732-2, 0732-3 show "clear." At time C the first sensor signal 0732-1 reads "blocked," as may indicate an object interrupting a first light beam for the first sensor 0724-1, while the second and third sensor signals 0732-2 and 0732-2 for the second and third sensors 0724-2 and 0724-3 still read "clear." At time D, the second sensor signal 0732-2 reads "blocked" while both the first and third sensor signals 0732-1 and 0732-3 read "clear." At time E, the third sensor signal 0732-3 indicates "blocked," while the first and second sensor signals 0732-1 and 0732-2 show "clear." Then at time F all three sensors 0724-1, 0724-2, 0724-3 generate sensor signals 0732-1, 0732-2, 0732-3 reading "clear," and likewise at time G sensor signals 0732-1, 0732-2, 0732-3 read "clear."

A comparison of FIG. 7 with FIG. 5 reveals that the sensor signals therein are visibly distinct between the two figures. Where in FIG. 5 up to three sensors report "blocked" at a time, in FIG. 7 only a single sensor registers as being blocked at any instant. Such an arrangement may reflect, for example, a smaller object entering the bin for FIG. 7 than for FIG. 5. Thus, as may be seen even simple sensors may enable distinguishing one object from another, such as an empty vial from a cap removed therefrom, given suitable arrangement of sensors and/or suitable interpretation of the signals therefrom.

Such discriminating ability may facilitate error rejection. For example, if a bin is to register only empty vials, rather than caps, other objects, etc., vials may be distinguished from caps (and so forth) through the specifics of the sensor signals generated. The signals in FIG. 5 may be taken as consistent with a vial, while the signals in FIG. 7 may be taken as inconsistent with a vial. In addition, the ability to identify (even if only approximately) certain incidental materials also may be applied to increase confidence. For example, if a patient is instructed to dispose of both the vial and the cap removed from that vial in a given bin, then both a signal consistent with the vial and a signal consistent with the cap within a brief time interval may provide redundant indication of medication use. If two pieces of packaging are expected and both are detected, then inferences that the medication has been taken may be made with more confidence than if only one were detected. By contrast, if two pieces are expected and only one is detected, this may be taken as an indication that medication was not taken, or at least that medication use is indeterminate, that some form of follow-up with the patient may be useful, etc.

Figure 8:
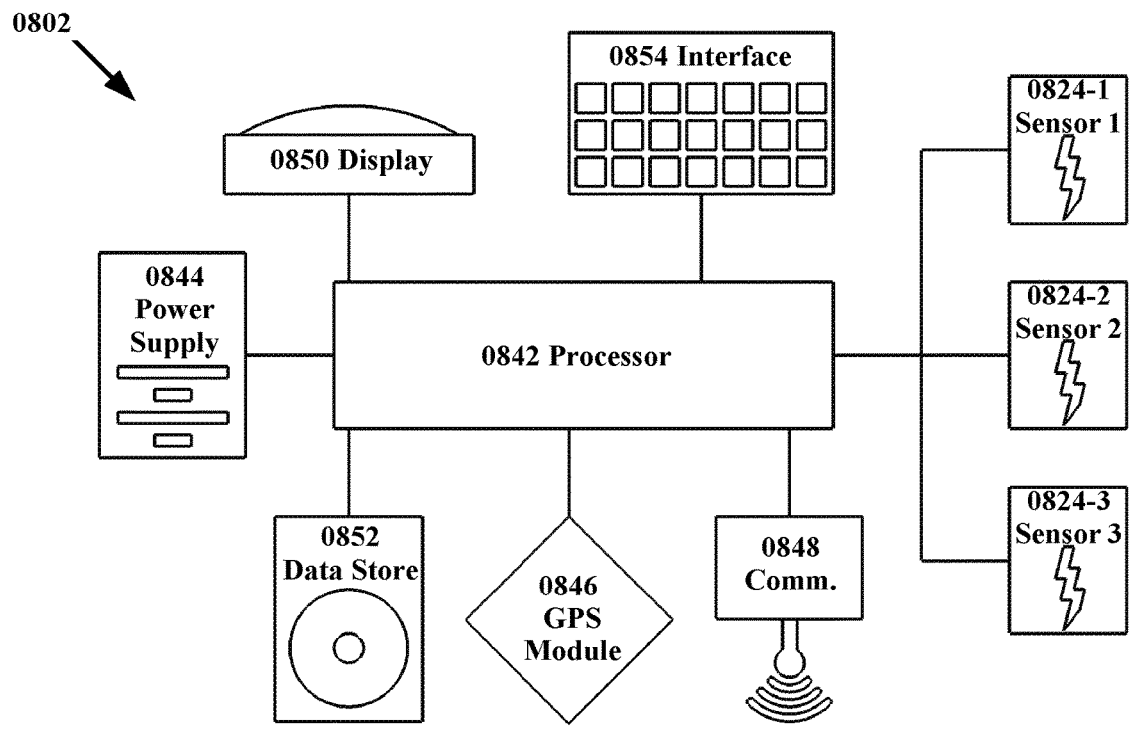
FIG. 8 shows elements of an example system, in schematic view.

Now with reference to FIG. 8, an example schematic illustrating certain functional elements of a bin system 0802 is shown. Not all elements necessarily will be present in all embodiments. Typically, a sensor may be present on or at least near a bin, and a processor may be in communication with the sensor (though as noted previously the processor may not be physically present on a bin). Certain other elements, while potentially useful and presented as examples, may not be required. In addition, while in practice the bin system 0802 may include structures such as a bin, lid chute, etc., such features may not interact with elements such as a processor, power supply, etc. in a manner as to be usefully illustrated in a schematic such as that shown in FIG. 8.

For illustrative purposes, FIG. 8 shows three sensors 0824-1, 0824-2, 0824-3 (though not all embodiments necessarily will have three), and a processor 0842 in communication with the sensors 0824-1, 0824-2, 0824-3. A power supply 0844 is shown, such as a battery and/or wall feed. FIG. 8 also shows an output element in the form of a graphical display 0850, for example so as to provide information to a patient such as a confirmation that a vial or other incidental material has been received and identified, a reminder to take a medication, a low-battery notice, etc. A user interface 0854 in the form of a keypad is shown as well, for example so as to enable a patient (or other person) to control, program, reset, etc., a bin and/or elements thereof. A data store 0852 is shown, for example as may store registered information, executable instructions, definitions and/or standards for identifying sensor signals, data regarding a medication regimen, the medication itself, the patient, the prescriber (if any), etc.

A communicator 0848 is also shown in FIG. 8; as noted, certain functions may be performed using cloud computing, and a communicator 0848 may facilitate communication between (for example) a sensor that is physically incorporated into a bin and cloud processing capability. In addition or instead, a communicator 0848 may convey information to some external recipient; for example, a pharmacy may be notified after empty vials representing 25 days of a 30-day prescription have been received, so as to request a refill, etc. Adherence information regarding the patient and/or medication also may be communicated, such as to a physician, manager of a clinical study, online database, etc. Additional elements also may be present, as may not be directly involved in functions described herein. As an example (though not limiting), a Global Positioning System (GPS) module 0846 is shown in FIG. 8 in communication with the processor 0842. The GPS module 0846 may provide location information, so that the processor 0842 may register where an empty vial was received as well as the fact of receipt, the time of receipt, etc. Such information may be particularly useful if a bin is mobile; for example, a diabetic may routinely carry with them a small sharps container as may serve as a bin so as to deposit used needles, empty insulin vials, and/or other incidental materials. Thus, the position of the bin may vary considerably, and information regarding the position of the bin when receiving needles (and potentially at other times as well) may be registered and utilized for further consideration.

Figure 9:
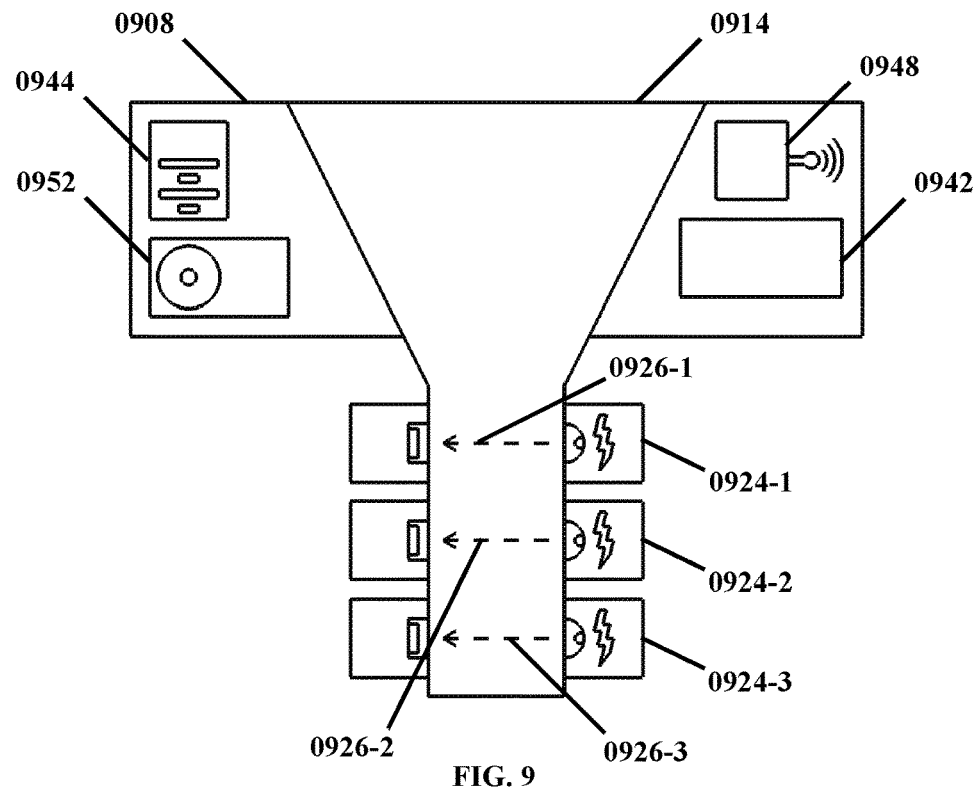
FIG. 9 shows an example bin lid independent of a bin body, with elements disposed within the bin lid, in side cross-section view.

Now with reference to FIG. 9, for certain embodiments it may be useful to incorporate some or all functional elements into one physical portion of bin, such as the bin lid 0908. A bin lid 0908 may be configured so as to be readily and/or removably engaged (e.g., through threads) with a variety of bin bodies (not shown in FIG. 9), just as a storage jar lid may fit many sizes and shapes of jar. (Conversely, a bin body may be configured so as to engage several types of bin lid.) In such case, the bin lid 0908 may be reasonably understood as a smart device unto itself, rather than necessarily as a component. For instance, the bin may be provided to a clinical study for use in evaluating the adherence of participants, with the study then selecting "dumb" jars to be engaged therewith as may be suitable for the particulars of that clinical study.

FIG. 9 thus shows an example of such a smart lid 0908. As may be seen, the lid 0908 includes a chute 0914 defining an aperture therethrough, with three sensors 0924-1, 0924-2, 0924-3 in the form of light beam sensors disposed at different vertical positions, such that light beams 0926-1, 0926-2, 0926-3 therefrom extend across the chute 0914. The bin 0908 also includes a power supply 0944 (e.g., a battery), a data store (e.g., a solid-state drive) 0952, a communicator 0948 (e.g., a Wi-Fi transceiver, Bluetooth transceiver, a Near Field Communication (NFC) transceiver, or some propriety transceiver), and an internal processor 0942 (e.g., a digital chip-based electronic processor). Thus, the lid 0908 may be functional as an independent entity, adapted to be engaged with dumb bin bodies (e.g., jars) as desired and performing smart functions as described herein regardless of what particular bin body may be present at a given time (and at least potentially even if no bin body is present).

Figure 10:
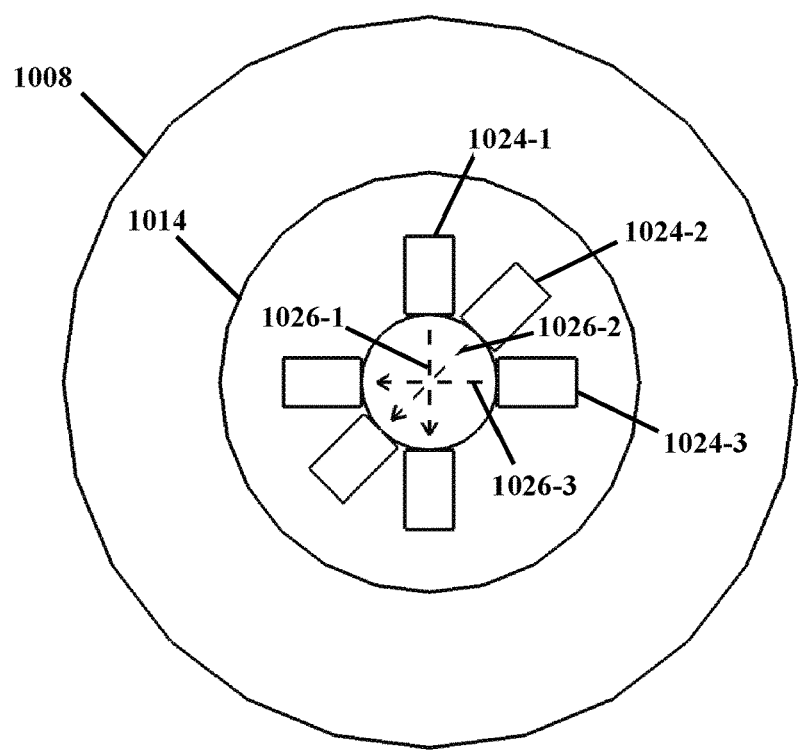
FIG. 10 shows an example bin lid independent of a bin body, with sensors disposed within the bin lid, in top-down cross-section view.

With reference to FIG. 10, a bin lid 1008 is again shown, this time in top-down view. The arrangement may be similar to that in FIG. 9, although in FIG. 10 only sensors 1024-1, 1024-2, 1024-3 and light beams 1026-1, 1026-2, 1026-3 therefor are shown disposed with respect to a chute 1014 for reference purposes (e.g., without a processor, etc., though in practice a processor and/or other components may still be present). While in certain other illustrations herein sensors are shown as being "in-line" for clarity, such an arrangement is not required. As may be seen in FIG. 10, the sensors 1024-1, 1024-2, 1024-3 therein are arranged at different angles with respect to the chute 1014. Such an arrangement may be useful for example in detecting objects that are flat, or otherwise not readily sensed from all directions. For example, a single-use vial may be formed via a process (e.g., injection molding of plastic) such that a flat, broad, elongate shape is convenient for manufacture (likewise, certain such shapes may be convenient for use, etc.). A thin vial viewed on-edge may not significantly interrupt a light beam; thus, if only one light beam sensor were present, or if all light beam sensors 1024-1, 1024-2, 1024-3 were oriented in the same direction, vials that by chance or design pass those sensors edge-on may not be identified. The arrangement in FIG. 10 shows one approach for addressing such concerns. Variable sensor orientation and/or position may also serve other functions (e.g., distinguishing different incidental items by shape, such as a cylindrical vial as distinct from a flat cap), and is not limited.

Figure 11:
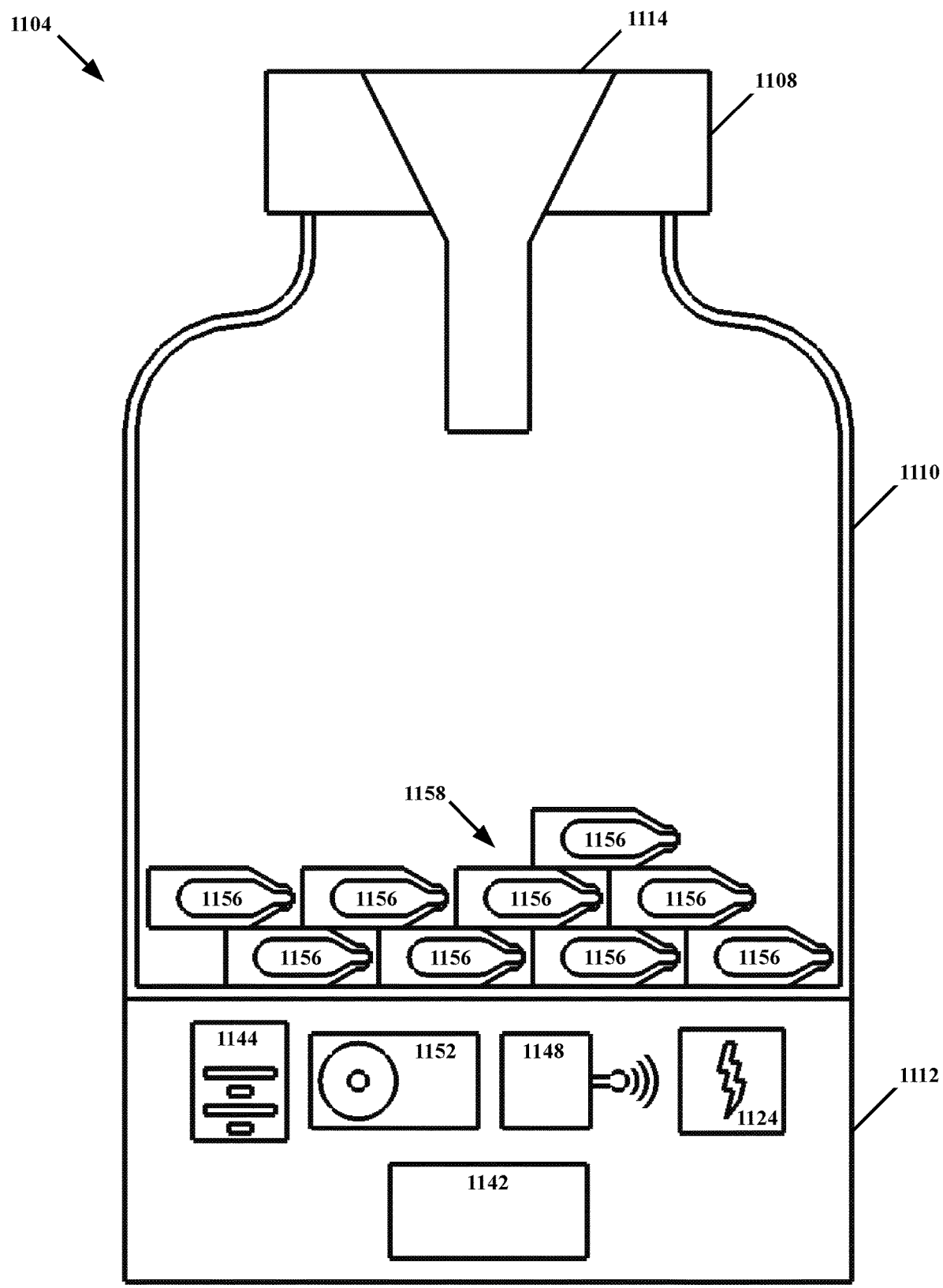
FIG. 11 shows an example bin with certain active elements in a base thereof, in cross-section.

Now referring to FIG. 11, as noted previously with regard to FIG. 10 some or all smart components may be incorporated into a lid; likewise, some or all smart components may be incorporated into a bin body, and/or into a base as may be engaged (removably or permanently) with a bin body. An example arrangement of such is shown in FIG. 11. As may be seen, a bin 1104 therein has a bin base 1112 engaged with a bin body 1110 that in turn has a bin lid 1108 engaged therewith; the bin body 1110 and bin lid 1108 are themselves "dumb," though physically at least somewhat similar in form to certain previously examples.

By contrast, the bin base 1112 includes a sensor 1124, processor 1142, communicator 1148, data store 1152, and power supply 1144. Thus, the bin base 1112 may serve as a simple add-on to an existing dumb container as may serve as a bin (e.g., the bin body 1110 combined with the bin lid 1108). However, disposing smart components in a bin base 1112 wherein that bin base 1112 is integral with the remainder of the bin 1104 is not excluded. Regardless, for an arrangement where only the bin base 1112 is smart it may be useful to select sensors that do not require a chute (though a chute is shown in FIG. 11 for illustrative purposes), such as an optical sensor aimed upward through from the bin base 1112 to/through the chute, an impact sensor that detects an impact of a single falling empty vial 1156, a weight sensor that detects the overall weight of an accumulation 1158 of vials, etc. so that "off the shelf" lids as well as jars may be readily used.

In addition, it is noted that sensors and/or other elements may perform other functions than those immediately related to identifying/registering incidental materials for medication. For example, if an acoustic sensor is available, characteristic sounds of a single-use eye drop vial being opened (e.g., "pops" as the cap is pulled away from the body) may be detected as well. Such an arrangement may provide further contextual events, e.g., a direct indication the vial has been opened and when, in addition to an indication that the empty vial has been discarded. This may be of particular interest if an acoustic sensor is used to determine receipt of the vial within the bin (e.g., by the sound as the vial is inserted, lands on the floor of the bin, etc.), as the same sensor(s) may be used for both tasks. However, use of distinct sensors (e.g., light beams for detecting receipt of the vial and acoustic sensors for detecting the vial being opened) also may be suitable.

While certain examples herein address eye drop medication and single-use vials therefor, it is emphasized that embodiments are not limited only thereto. Other medications, incidental materials, etc. also may be suitable for consideration. In addition, while used containers may be referred to herein as an example of incidental materials, this also is not limiting. A hypodermic needle, while not necessarily a container for medication or anything else (e.g., rather being at least arguably a vehicle or delivery system), still may be sensed and identified as incidental material. Furthermore, the use for medical applications itself should not be understood as limiting. While certain examples herein address medical uses, embodiments may sense, identify, and/or consider non-medical materials. Any material made available incidental to any action may at least in principle be suitable, including but not limited to empty non-medical containers, or even food waste, etc.

In addition, it is noted that receiving incidental materials, and/or other contextual events, may not provide and may not be required to provide exact data regarding the use of medication. That is, a patient may not immediately dispose of an empty vial. Not all medications are highly time-sensitive; it may be sufficient to verify adherence simply by providing authenticated data that a patient takes their medication once per day, regardless of the time. Furthermore, even for medications that are time-sensitive it may not be necessary to know exactly when a patient used a medication in order to make use of authenticated data indicating that the patient is using that medication. For example, knowing how many hypodermic needles or vials of insulin a person with diabetes uses per day or per week may be useful in validating adherence and/or other matters, even if the precise times that the patient administered the medication are not known. Likewise, if a patient is to take a given medication three times per day, and each evening deposits three empty blister packs, this may be useful in monitoring adherence regardless of whether the exact times the medication were taken are known. Thus, it is not necessary for the detection of incidental materials to correlate precisely with medication use, for all embodiments.

Furthermore, the times of disposal of waste may for example exhibit patterns; even if those patterns do not perfectly represent times of use, or even if the underlying causes/meanings of the patterns themselves are not understood. Even for a pattern that appears arbitrary, variations in that pattern may be of interest, representing changes in how a patient is taking a medication, etc. For at least certain instances knowing that a patient is taking a medication in a consistent manner may be of use (e.g., the number, arrangement, etc. of received vials this week is similar to last week), even if it cannot be determined precisely when the patient is taking that medication. In addition, certain patterns may be identified (even if aspects thereof may not be fully understood) as corresponding to practical considerations. For example, a certain pattern of disposing of empty vials may be associated with deliberate attempts to "fool" the smart bin in some manner. Even if the reasons underlying the existence of such a pattern are not known, if a pattern can be connected with a phenomenon that generates that pattern, detecting the pattern and changes therein may be useful in itself (e.g., a pattern known from experience to be associated with fraud may be detected and considered as an indication of possible fraud, even if the reason for fraudulent users exhibiting that pattern are unknown). Moreover, information may be determined simply from general behavior of a patient with regard to discarding incidental materials. For example, if a patient is highly conscientious in depositing their empty eye drop vials, it may be reasonable and/or useful to infer that the patient likely may be similarly conscientious in taking the medication as well.

In addition, other information may be obtained based on what is discarded from a medication, without knowing even approximately what time the medication was taken. For example, certain medications may produce severe or even dangerous side effects if taken close together. If empty blister packs for two different pills are deposited in a bin close together, this may indicate that the medications were taken together. If taking those two pills together is contraindicated, the information that they have been taken together may be of use. (For instance, the patient may be alerted with a reminder, their physician may be advised, etc.) Conversely, if two medications work best when taken together, and incidental material from those materials was received in a bin together, this may be an indication that the medications were indeed taken together.

Certain previous examples have addressed the entry of incidental materials into a bin (or other enclosure). For example, FIG. 4A through FIG. 4H show the entry of incidental material in the form of a used vial into a bin in the form of a lidded jar, that jar lid defining a chute therein and sensors in/proximate the chute. However, while it may be suitable for at least certain embodiments to consider the entry of incidental materials, it may be suitable to consider the exit of incidental materials in addition or instead. For example, considering the configuration in FIG. 4A through FIG. 4H the light-beam sensors therein may detect a vial entering the bin via the chute; however, such light-beam sensors also may be suitable for detecting a vial exiting the bin via the chute. For example, if the bin were inverted so that a vial therein may exit under the force of gravity, light beam sensors as are illustrated therein may produce clear and/or blocked values as may be interpreted as indicating that the vial has left.

Certain structural and/or functional variations from what is shown in FIG. 4A through FIG. 4H may be useful for embodiments adapted to detect incidental material exiting a bin. For example, where the chute in FIG. 4A through FIG. 4H is shown to be broad at the top thereof tapering to be narrow at the bottom thereof (e.g., so as to facilitate convenient deposit of vials into the bin), a chute for an embodiment adapted to detect exiting incidental materials may be broad at the bottom thereof in addition or instead.

Also, while typically it may be expected that the amount of incidental material introduced into a bin at a given time may be small—e.g., one vial from medication taken shortly before, a few vials from medication taken over the course of a day, etc.—when emptying vials from a bin a larger number of such vials may exit simultaneously and/or in rapid succession. In such instance, it may be useful for sensors to provide more specific output than "clear" and "blocked." For example, some number of levels of transmitted light, e.g. a scale of 0% through 100% in 10% increments, may facilitate the identification of multiple used vials exiting a chute together. That is, if a single vial reduces the light intensity detected by a light beam sensor by 10%, then a reduction of 20% may indicate two vials are exiting together (e.g., overlapping, with both vials between the beam source and beam receiver). Sensor signals with such finer distinction may be visually more complex than the illustrative examples presented in FIG. 5 and FIG. 7, but finer distinction in light levels (or other sensed phenomena) also may facilitate gathering of additional data. (Although FIG. 5 and FIG. 7 show simple binary sensor signals for illustrative purposes, it is noted that such higher distinction also is not excluded for arrangements that only detect incidental materials entering a bin, as opposed to exiting the bin.) Similarly, capacitive sensors, acoustic sensors, etc. also may be suited for finer distinction than simple binary signals, with at least potential to distinguish multiple vials exiting at once, and/or other phenomena.

With regard to consideration of exit data, detecting the exit of materials may for example provide at least some degree of independent confirmation of those materials having been inserted into the bin. That is, if vials exit a bin when the bin is emptied, it may be presumed that those vials at some point were inserted into that bin. Thus, if (for example) 31 vials have been detected being inserted and 31 vials are also detected being removed, a greater confidence in the overall count of vials may be obtained. Conversely, if the number of vials detected to enter is not the same as the number detected to exit, it may be considered that some error is taking place, e.g., sensor failure, power failure, some other systematic problem, deliberate fraud, etc. In addition, while emptying a bin once a month may not indicate when individual doses have been taken, knowing that a user has taken 31 doses in 31 days may in itself be useful information in tracking compliance.

At least in principle, such exit detection also may be considered in dispensing medication containers or similar. For example, a single bin may be configured with a compartment for storing individual full medication vials and dispensing those vials therefrom, and a compartment for receiving and accumulating used medication vials. Such configuration may utilize the same sensors, chutes, etc. Thus, detection not only of used containers (or other incidental materials) exiting a bin but also of unused containers may be facilitated and considered, in at least certain embodiments.

Additional data besides the entry and/or exit of incidental materials also may be considered for at least some embodiments. For example, consider a weight sensor used to track the cumulative weight of an accumulation of used vials (e.g., as may be consistent with FIG. 11). If some residual liquid medication is present in the used vials, then the total weight for an added vial may be greater than the weight of the vial itself (exclusive of medication). Likewise, the weight of a used vial may gradually decrease as liquid evaporates and vapor therefrom exits the bin via the chute. Thus, through the use of a weight sensor (e.g., a piezoelectric force sensor) some value (or at least some approximation) of how much medication remained in each vial at the time of disposal, or in a group of used vials in aggregate, etc., may be determined. In turn, if the weight of medication in unused vials is known, the weight of medication removed from those vials may be determined from the weight of the used vials; consequently. the amount of medication being dispensed may be determined. For medication regimens wherein dosage is a factor, data regarding how much medication is dispensed may be useful in evaluating compliance with the regimen (and/or in making other determinations).

As an additional comment, while certain examples herein may refer to a bin as performing a function of sensing, identifying, and/or registering information regarding the use of medication, other functions are not excluded. For example, a "sharps" container as may serve to safely enclose hypodermic needles and/or other materials; a bin as described herein is not prohibited from also being configured to secure medical sharps, etc. Other functions also may be carried out, and are not limited.

Again with reference to FIG. 11, as may be seen therein functional elements thereof (e.g., processor 1142, data store 1152, sensor 1124, etc.) may be grouped together within a bin base 1112. Although in the arrangement shown in FIG. 11 the grouping thereof is shown as being part of and/or physically engaged with the remainder of the bin 1104, this is not necessarily required for all embodiments. For example, a bin base 1112 may be separate from and/or removably engaged with a bin 1104 overall, such that the bin base 1112 may be used with different bins (e.g., different sizes/models of bins for different incidental materials, replacement bins after one bin is filled, etc.).

In addition, at least certain functional components as shown in bin base 1112 may be physically distant and/or distinct from the bin 1104 overall. For example, a smart phone or smart speaker may have suitable acoustic sensors for detecting the impact of vials within a bin. If it may be considered that a smart phone is typically carried by a person depositing used vials, or that a smart speaker may be in the same or a nearby room to a bin, it may be that the smart phone/smart speaker is "within earshot" of the bin, even if not in physical contact with the bin at the time a vial is dropped. Further, certain embodiments may incorporate mechanisms to facilitate or enhance such remote sensing. For example, a bin may be constructed with a chute having a mechanical "noise maker" therein, such that when a used vial is deposited therein a characteristic sound is produced as may be detected by a smart phone or other device. Thus, while certain examples herein show "smart" components (e.g., processors, sensors, etc.) disposed on or physically engaged with a bin, embodiments wherein the smart components are present on some other device such as a smart phone or smart speaker (or smart TV, etc.) also may be suitable. In such manner, a bin may function as a smart device, even if physically "dumb" (e.g., active smart components such as the processor and/or sensors are offloaded from the bin itself onto a different and potentially remote device). The particulars regarding arrangement and/or position of functional smart components are not limited, and may vary considerably.

Figure 12A:
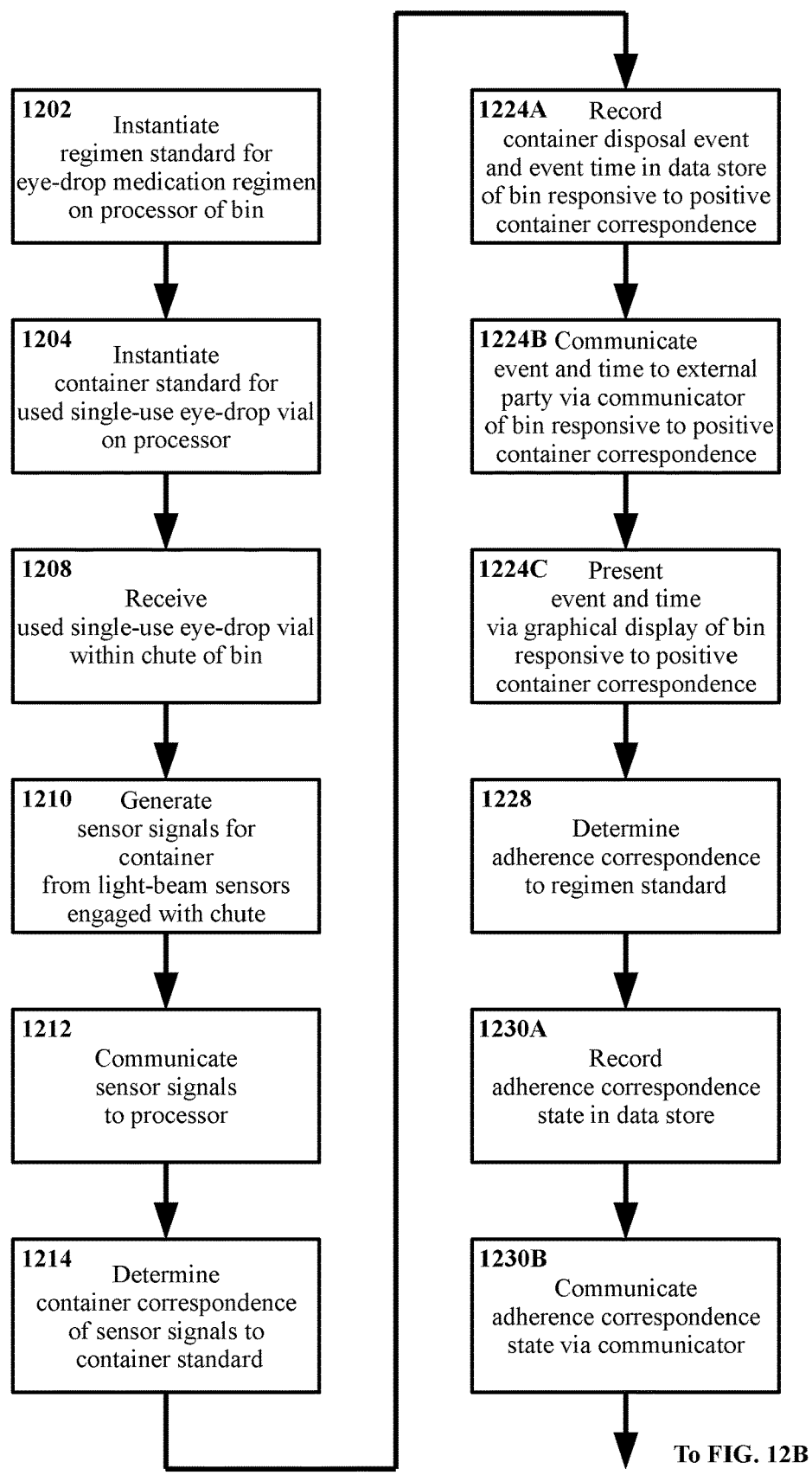
FIG. 12A and FIG. 12B show an example method for authenticating use of eye-drop medication through considering deposition of used single-use vials, in flow-chart form.
Figure 12B:
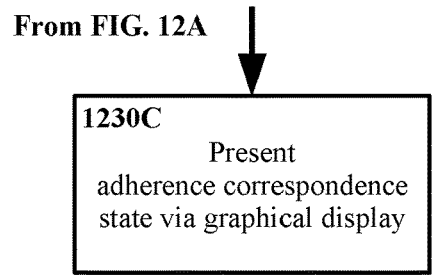

Now with reference to FIG. 12A and FIG. 12B, therein an example method is shown for smart authentication of medication use while utilizing non-smart medication containers. The example of FIG. 12A and FIG. 12B is presented in relatively concrete terms, e.g., light-beam sensors, a single-use eye-drop vial, a processor that is part of a bin, etc. Such specifics are presented for explanatory purposes, but should not be considered limiting.

In FIG. 12A, a regimen standard for an eye-drop medication regimen is instantiated 1202 onto the processor of a bin, such as (though not limited to) a bin as shown in FIG. 1 or FIG. 11. Typically, the regimen standard may define features such as what the medication regimen is, what constitutes adherence therewith, some range of degrees of acceptable adherence, what degree of adherence is acceptable, etc. As a more concrete example, a regimen standard may specify that empty vials are to be deposited (and thus medication may be presumed to be taken) at 9 AM and 9 PM nominally each day, that a range of plus-or-minus 30 minutes is considered as "on-time," and to consider only vials deposited within the specified time windows as indicating adherence, and for an overall degree of adherence to constitute a percentage value of adherent events (as opposed to late, missing, etc.). Thus, if over the course of 10 days 17 of 20 windows of exhibit vial detections therein and 3 windows do not exhibit vial detection therein, adherence would be determined as being 85%. It is noted that the above is an example only; arrangements may be more or less complicated, may weight factors rather than simply assigning yes/no values (e.g., a late vial deposit may contribute to an adherence value but may weighted to count less than an on-time vial deposit), may consider missed vials as distinct from early/late vials, may make provision for excess vials (e.g., 3 vials deposited in 24 hours rather than the nominal two vials), may incorporate environmental information or other data, etc. The form and contents of a given regimen standard may vary considerably, and is not limited. In particular, although as shown in FIG. 12A the regimen standard may take the form of executable instructions and/or data instantiated onto a processor, this also is not limiting.

A container standard for a used single-use eye-drop vial is also instantiated 1204 onto the processor. Typically, the container standard may define features such as what sensor signals are to be considered indicative of a used vial passing through the chute of a bin. For example, for light-beam sensors and a vial as shown in FIG. 4A through FIG. 4H, sensor signals may be expected to resemble those shown in FIG. 5, but not those signals shown in FIG. 7. As a more concrete example, a container standard may specify that top, middle, and lower light-beam sensor signals should indicate a switch from clear to blocked in sequential order, and then indicate a switch from blocked back to clear also in sequential order (e.g., as shown in FIG. 5). However, this is an example only. Factors other than ordering of features in sensor signals may be considered, for example the length of time each of top, middle, and lower light-beam sensors are blocked, the times between when the top and middle sensors and middle and lower sensors are blocked, etc. Also, as noted sensors may return signals not limited only to clear and blocked states, and thus container standards may refer to levels as opposed to binary states, etc. The complexity and/or configuration of a container standard is not limited. In particular, although as shown in FIG. 12A the container standard may take the form of executable instructions and/or data instantiated onto a processor, this also is not limiting.

With regard to steps 1202 and 1204 collectively, although the regimen standard and container standard may to at least some degree overlap and/or interrelate, in practice the functions thereof may be distinct. In colloquial terms, a container standard defines what a used vial "looks like" (e.g., what sensor readings indicate a used vial being deposited in the bin), while a regimen standard defines when, where, at what intervals, etc. used vials are expected. However, some relationship may exist between such factors e.g., when used vials are expected to be detected (thus, when a medication is to be taken) and what the empty vial looks like both may be at least partially a function of the medication itself.

Continuing in FIG. 12A, a used single-use eye-drop vial is received 1208 within a chute in the bin. Deposit of such a vial has been previously shown, e.g., in FIG. 4A through FIG. 4H. The particular manner and/or mechanism by which the vial (or other incidental material) enters the bin is not limited, and may vary considerably based on factors including but not limited to the form of the medication and/or incidental materials (e.g., empty blister packs from pills, empty squeeze vials for eye-drops, etc.).

Sensor signals are generated 1210 by light-beam sensors engaged with the chute for the deposited eye-drop vial. Typically though not necessarily such signals may be electrical, e.g., low-current 5-volt data signals. However, the form and nature of the signals are not limited (nor are the form and nature of the sensors themselves, the number thereof, the arrangement, etc.). The sensor signals are communicated 1212 to the processor. The manner of communication is not limited, but may depend at least in part on the specifics of the sensors and/or processor. For example, in an arrangement wherein the processor is a cloud processing function (as opposed to a discrete physical device) the sensors may communicate wirelessly.

A determination is made 1214 as to whether the sensor signals correspond with the container standard, such that those sensor signals may represent a used container being deposited within the bin. The form and/or particulars of the determination 1214 may vary, for example depending on the nature of the container standard for a given embodiment. Typically, though not necessarily, the container standard itself (as instantiated 1204 previously in FIG. 12A) may specify what is required for sensor signals to be considered as representing a container being deposited, while the container correspondence determination 1214 may evaluate whether/to what degree a given sensor signal (or group thereof) satisfies the container standard.

As a simple example, a container correspondence determination 1214 may be positive or negative, that is, sensor signals either do satisfy a container standard or those sensor signals do not satisfy that container standard. However, while such a binary approach may be suitable for some embodiments, embodiments are not limited thereto. For example, some "gray area" may be defined, wherein correspondence may be considered as likely but not necessarily definitive. Confirmation may be expressed along some scale, e.g., percent confidence, various classes ranging from weak to strong indications, some numerical scale (e.g., 1 to 10), etc. For illustrative purposes the example in FIG. 12A and FIG. 12B addresses a binary determination, e.g., positive or negative.

However, although not all container correspondence determinations 1214 necessarily will be binary, in terms of follow-up actions as may be based on the outcome of the container correspondence even arrangements not explicitly binary may at some point be reduced to or considered as binary, e.g., either a follow-up action is taken, or is not taken. Thus in at least some sense it may be reasonable to refer to a "positive" outcome even if the container correspondence determination 1214 itself is not binary, e.g., the determination yields a confidence percentage, and anything over 85% confidence triggers a particular follow-up action. However, not all potential follow-up actions necessarily may be based on the same determination result. For example, any sensor signals that provide more than 50% confidence that a container has been deposited may be stored (or otherwise registered), while only sensor signals that exceed 75% confidence subsequently are considered in determining adherence. For such an example, borderline events may be logged (e.g., for further examination later) without necessarily affecting adherence determinations in the immediate term. Thus, while certain examples herein (including that shown in FIG. 12A and FIG. 12B) may refer to positive/negative determinations, this should not be understood as limiting embodiments only to such binary arrangements.

Continuing in FIG. 12A, responsive to a positive container correspondence (as determined 1214), a container disposal event and the event time thereof is recorded 1224A in a data store of the bin. That is, if it is considered that a used vial has been deposited in the bin (based on sensor signals, etc.), that event of disposal/deposition is recorded along with the event time. Typically, the event time may be considered as the time at which the sensor signals are generated, though this may vary among embodiments (e.g., the time the sensor signals are received in the processor, the time the determination is made by the processor, etc., may be used instead). Event time may for example be determined by a chronometer on the processor, though other sources also may be suitable.

Also responsive to a positive container correspondence, the event and time are communicated 1224B to some external party via a communicator of the bin. For example, in a clinical study each disposal event and disposal event time may be forwarded to a database tracking medication use for the study. Alternatively, a physician, pharmacist, or caregiver may be notified. As yet another alternative, the medication user's own smart phone (or similar device) may be contacted with the event and event time, for example so that the user may readily look up when they took their most recent dose of medication. Other parties also may be suitable, and are not limited. Similarly, many forms of communication (e.g., hard-wired signals, text messages, e-mails, Wi-Fi transmissions, etc.) may be suitable, and are not limited.

Again responsive to a positive container correspondence, the event and time are presented 1224C on a graphical display of the bin. For example, a given embodiment of a bin may include a display screen as may show that medication was most recently taken at a particular time. Alternately, simple visual telltales may be suitable, e.g., a green LED when the user has taken medication, a yellow LED when the user is due but has not yet taken the medication, and a red LED indicating that the user has missed a dose (or otherwise is non-adherent). In addition, while the example of FIG. 12A refers specifically to graphical displays, other output mechanisms may be suitable, such as acoustic systems that deliver audible chimes, spoken words, etc. The particulars of how and by what mechanism the event and time may be outputted is not limited.

Steps 1224A, 1224B, and 1224C may be in at least some sense similar to one another, at least insofar as all such steps are responsive to the container correspondence determination 1214 and all address some action carried out with a disposal event and a time therefor. Collectively and more generally, steps 1224A, 1224B, and 1224C may be considered as parts or forms of registration of the event and time, that is, some manner by which the event and event time are noted or recognized. As shown in FIG. 12A, registration may include recording data, communicating data to other parties, and displaying data, but registration does not require any or all such, nor is registration limited only thereto. In various embodiments, data may be only displayed but not recorded or communicated, or some other registering action may be taken in addition to or in place of recording, communicating, or displaying the disposal event and event time. Thus, while FIG. 12A presents an arrangement with several explicit examples of registration, it may be equally suitable to refer to registration generally, rather than specifying or requiring a particular type of registration.

Continuing in FIG. 12A, an adherence correspondence determination is made 1228 as to whether and/or to what degree the regimen standard is being followed. As noted with regard to container correspondence, the regimen standard typically may specify when/how a medication is to be taken, while the adherence correspondence determination 1228 may address to what degree medication is being taken according to that regimen standard (or at least, insofar as medication use may be inferred from the deposition of empty vials or other incidental materials). As with container correspondence, adherence correspondence may be but is not required to be determined in binary form, e.g., adhering or not adhering. Thus, an adherence state may be "adherent" or "not adherent" but alternatively may be "93% adherent," "good adherence," "green" (or yellow, or red), etc.

In addition, it is noted that adherence correspondence determinations are not limited with regard to how many disposal events are considered. In certain embodiments it may be useful to only consider a single event, e.g., has the user taken their most recent dose of medication on time? In other embodiments it may be useful to consider multiple events, for example all events (and times) since the medication was prescribed, a running series of events over the past 30 days, or some other arrangement. In addition, adherence determinations and/or standards therefor (like correspondence determinations) may be weighted or otherwise tailored, e.g., a medication prescribed to address a condition aggravated by sunlight may be less strict for events in winter than in summer, etc.

Still with reference to FIG. 12A, the adherence state is recorded 1230A in the data store of the bin. The adherence state also is communicated 1230B via the communicator, and in continuing in FIG. 12B the adherence state is further presented 1230C via the graphical display. Collectively, recording 1230A, communicating 1230B, and presenting 1230C the adherence state may be considered to represent registering the adherence state. Registration is not limited only to the examples presented in FIG. 12A and FIG. 12B. In addition, it is noted that even though the arrangement in FIG. 12A and FIG. 12B is deterministic with regard to types of registration—that is, the adherence state is recorded 1230A, and is communicated 1230B, and is presented 1230C—this too is not limited. For example, in a given embodiment the adherence state may be recorded 1230A in all cases, but may only be communicated (e.g., to a medical professional) if adherence falls below some threshold (e.g., 70% adherence). (Such variability also may apply to other registrations, e.g., certain forms of disposal event and time registration may be carried out in all cases, while others may be conditional, etc.)

In addition, while event and time registration are referred to in FIG. 12A as being responsive to positive determinations that an event has happened (that is, that a used vial was deposited in the bin), it is noted that registration of adherence is not shown as being responsive to a particular event. Although registering adherence in response to some condition or event is not prohibited, neither is registration of adherence necessarily required to be responsive to a condition or event. Thus, adherence may be determined (for example) periodically, e.g., once per day, whether or not a disposal event has been detected during that period. As may be understood, in determining adherence, it may be significant to note that the user is not taking their medication at all, in which case there may be no events to which to respond. (With regard to event registration being responsive to an event being detected, it is noted that if no event is detected, then there is nothing to register. However, in at least some embodiments the lack of a disposal event may be registered even then.)

Figure 13:
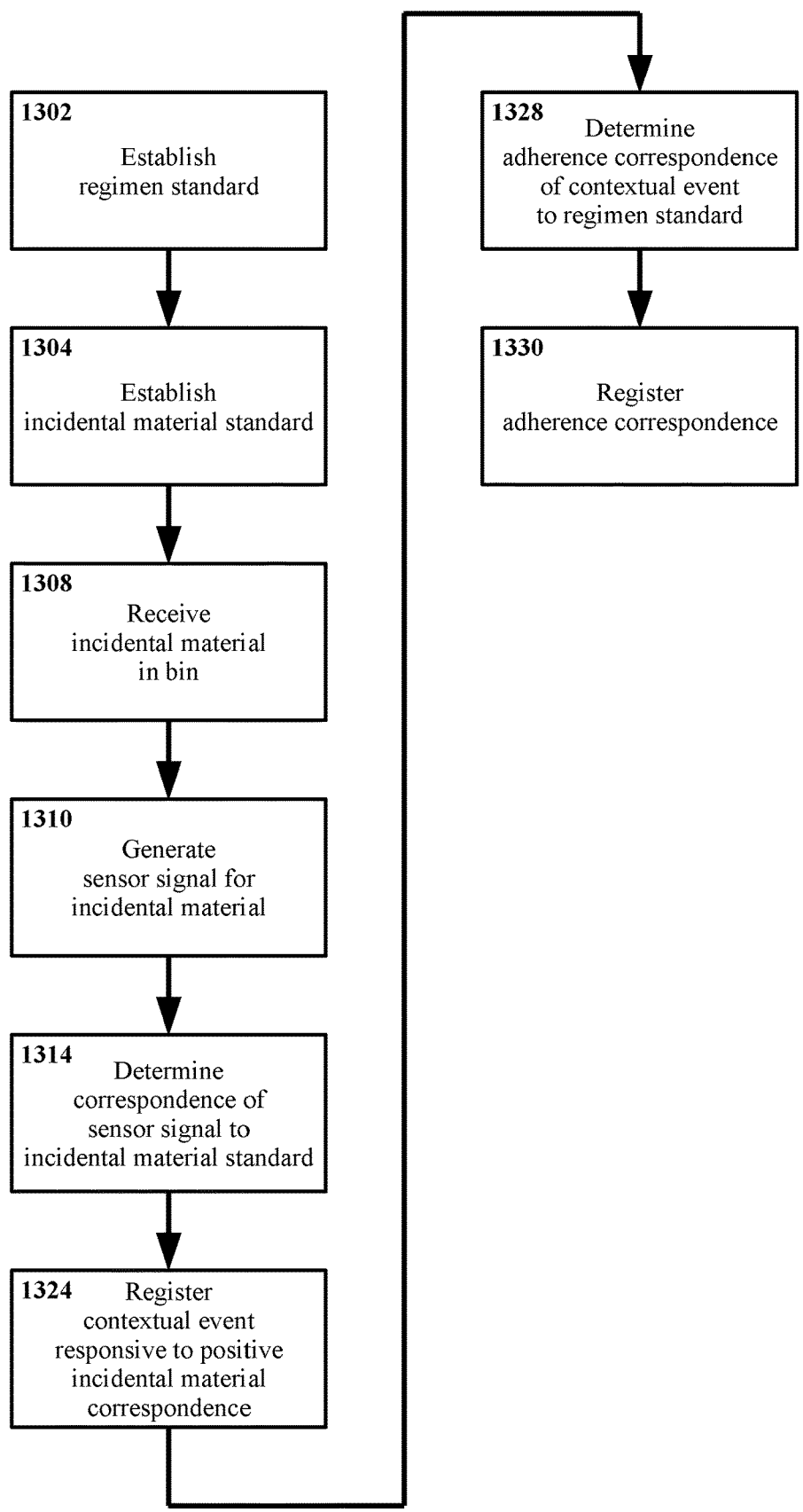
FIG. 13 shows an example method for smart authentication of medication use through considering non-smart incidental materials associated therewith, in flow-chart form.

Turning now to FIG. 13, another example method is shown therein. Where the example in FIG. 12A and FIG. 12B is presented in relatively concrete terms, that of FIG. 13 is somewhat more general in approach. Even so, the arrangements of FIG. 13 are not limiting.

In FIG. 13, a regimen standard is established 1302. Typically, though not necessarily the regimen under consideration may be a medication. However, regimens also may be established for other products and/or services. One example (though not the only one) may be skin lotion. A regimen may be defined for a moisturizing skin lotion or sunscreen lotion, e.g., each night between 10 and 11 PM for moisturizing lotion, every two hours during sun exposure for sunscreen lotion, etc. Regimen standards for eye-drop medication were previously described with regard to FIG. 12A, and while certain variations may manifest specific to varying products or services, regimens and regimens standards in general may be understood similarly. In addition, it is noted that in FIG. 13 the regimen standard is not necessarily required to be established 1302 on a processor that is part of or otherwise specific to a bin. Some other approach, for example establishing 1302 a regimen standard in a processor in a distinct device such as a smart phone, smart speaker, etc. also may be suitable.

An incidental material standard is established 1304. Although at least potentially somewhat similar to the container standard referenced in step 1204 in FIG. 12A, the incidental material standard established 1304 in FIG. 13 does not necessarily define or otherwise address a used container. Rather, an incidental material standard may address any one (or more) incidental materials as may serve to indicate that some contextual event has taken place. A container standard may be considered as a subset of an incidental material standard, at least insofar as a used container is a subset of incidental materials. However, incidental materials may refer to objects/features other than containers, for example packaging, applicators, caps, security seals, etc.; likewise, an incidental material standard may address what indications (e.g., sensor signals) may be expected to correspond with that incidental material. Similarly, depositing a used vial may be considered as a subset of a contextual event, that is, depositing a used vial may be a type of event as may be taken to indicate medication has been taken; however, contextual events are not necessarily limited to depositing vials (nor to being indications that medication has been taken).

Continuing in FIG. 13, incidental material is received 1308 in a bin. For example, a used vial, a hypodermic needle, or some other material related but incidental to an event of interest (e.g., taking a medication) may be received 1308. At least one sensor signal is generated 1310 from at least one sensor for the incidental material. For example, a light beam sensor may exhibit a change in beam strength as the incidental material obstructs the light beam, a capacitance sensor may exhibit a change in capacitance as the incidental material passes through or proximate the sensor, etc.

An incidental material determination is made 1314 regarding correspondence of the sensor signal(s) to the incidental material standard. For purposes of explanation, incidental material correspondence with regard to FIG. 13 is again referred to as either positive or negative, though as noted such binary determinations are not necessarily required for all embodiments. In addition, it is noted that communicating the sensor signal is not explicitly shown in FIG. 13; if sensor signals are generated 1310 and are used in a determination 1314, it may be presumed that the sensor signals in some manner came to be available where the determination is made.

Responsive to a positive incidental material determination, a contextual event is registered 1324. For example, as described with regard to FIG. 12A and FIG. 12B, various information may be stored, communicated, displayed, etc. Still with reference to FIG. 13, an adherence correspondence determination is made 1328 with regard to the regimen standard, e.g., some evaluation is performed as to whether the use of medication or other activity (as inferred from the detection of incidental material associated therewith) is in keeping with a regimen specified therefor. The adherence correspondence (for example, a percentage, good/mediocre/inadequate, etc.) is registered 1330.

Figure 14:
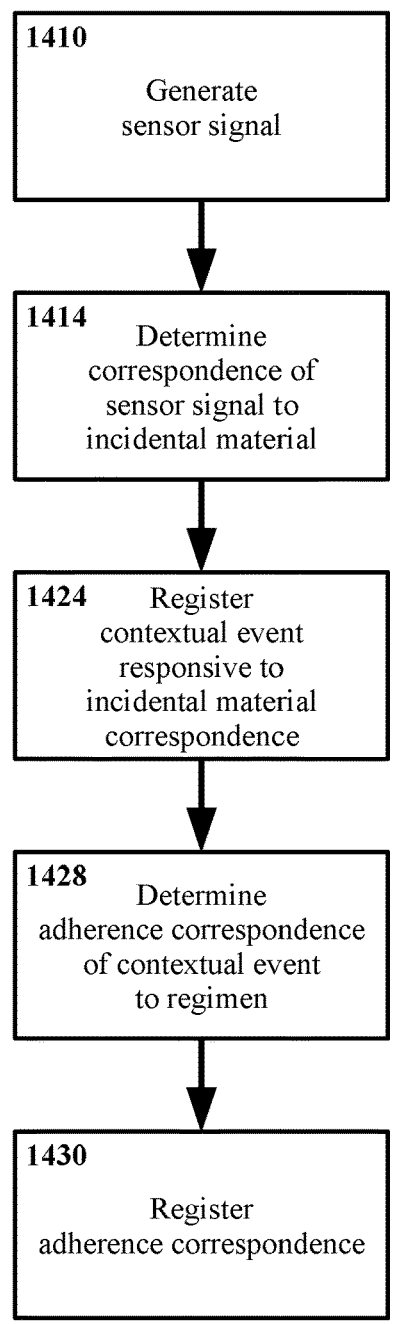
FIG. 14 shows an example method for smart authentication of medication use through considering non-smart incidental materials associated therewith, from a perspective of a system therefor, in flow-chart form.

Turning now to FIG. 14, another example method is shown therein. In the arrangement of FIG. 14, the method therein is presented in a manner as may represent the point of view of a bin, bin monitor/remote, or similar device, specifically with regard to active function thereof for an incidental event (as opposed to programming, assembly, etc.). Thus, instantiating or otherwise establishing standards is not explicitly shown (e.g., standards may be instantiated onto a processor well before the bin is used, though other arrangements may be suitable), nor is the receipt of incidental material into the bin (e.g., since the bin may not "do anything" in a positive sense, merely passively receiving material placed therein, though again other arrangements may be suitable).

In FIG. 14, at least one sensor signal is generated 1410. Typically, such sensor signal(s) may be of interest when referring to a particular type of incidental material, e.g., one as may be taken to infer that a medication has been taken. However, in practice not all sensor signals as may be generated necessarily will reflect the incidental material of interest. That is, some sensor signals may be generated for other interactions, e.g., dropping a cap from a vial into a bin when the material of interest is the vial itself. Other sensors may be generated for a curious child or pet sticking a finger into a bin, deliberate physical manipulation of the bin (such as initial set-up, moving the bin to a new location, etc.), sensor self-tests, various errors, etc. It is not required that all sensor signals generated 1410 (or likewise in other examples herein) will be or must be indicative of the contextual event of interest.

The correspondence of the sensor signal(s) to incidental material is determined 1414. Typically, though not necessarily, some standard may be established (e.g., as in FIG. 12A) and the determination 1414 based thereon. However, the particulars for how the determination 1414 may be carried out are not limited, and arrangements that do not utilize a material correspondence standard also may be suitable.

Responsive to the determination of incidental material correspondence in 1414, a contextual event may be registered 1424. As noted previously, the determination 1414 may not necessarily be binary, e.g., restricted to only positive or negative. Thus, the arrangement shown in FIG. 14 is not limited to a binary determination. Typically, if the determination 1414 is that incidental material has been deposited, is likely to have been deposited, etc., the contextual event will be registered 1424; while otherwise a contextual event will not be registered. However, as noted previously the determination 1414 and registration 1424 may vary among embodiments.

Correspondence of some or all contextual event(s) as may be identified as having occurred relative to a regimen is determined 1428. As noted previously, an absence of contextual events also may be considered in determining 1428 adherence correspondence (e.g., if a user isn't taking medication at all and there are no events to consider, some determination 1428 of adherence still may be carried out, though adherence presumably may be evaluated as poor, nonexistent, etc. in such instance). The adherence correspondence as determined 1428 is also registered 1430.

Figure 15:
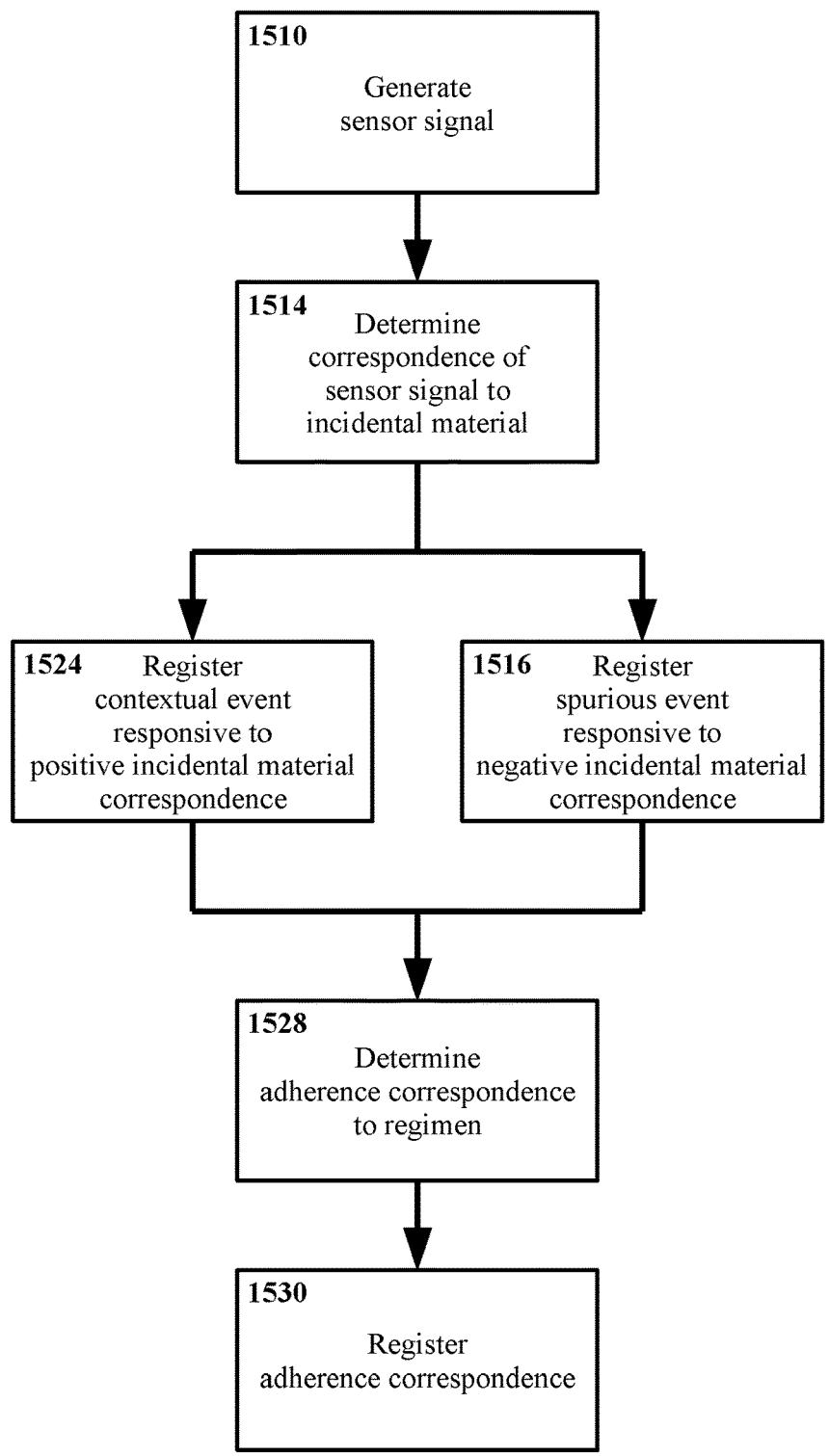
FIG. 15 shows an example method for smart authentication of medication use through considering non-smart incidental materials associated therewith, exhibiting spurious even registration, in flow-chart form.

A number of variations may be incorporated into various method embodiments (and/or similarly into apparatus embodiments therefor). FIG. 15 shows one such variation, with attention to determination and/or registration not only of contextual events as may be of interest but also determination and/or registration of other, e.g., spurious, events. For example, an embodiment may identify and register both used vials and also other (irrelevant) debris as may be deposited into a bin.

In FIG. 15, a sensor signal is generated 1510. (As noted with regard to certain other examples herein, additional steps, e.g., instantiating instructions, standards, etc. may take place, but at least for explanatory purposes may be inferred rather than being shown explicitly). It is noted that the sensor signal generated 1510 is not presumed to be a sensor signal corresponding to a given contextual event as may be of interest, such as the deposition of a used medication container or other incidental material into a bin. While it may be possible that the sensor signal corresponds with such a contextual event, the sensor signal may be generated 1510 from other phenomena, e.g., handling of such a bin, deposition of other materials therein, sensor noise or error, etc. Pursuant thereto, a determination is made 1514 as to whether (and/or to what degree, etc.) the sensor signal does correspond to incidental material.

Responsive to a positive determination of correspondence in step 1514—the sensor signal does correspond to incidental material being deposited—a contextual event is registered 1524, e.g., recorded in a data store, presented via a display, etc. Alternately, responsive to a negative determination—the sensor signal does not correspond to incidental material being deposited—a spurious event is registered 1516. The manner and content of registration 1516 of a spurious event may vary considerably, as previously noted with regard to registration of contextual events in other examples herein. For example, the fact of a spurious event, the time thereof, etc., may be recorded, displayed, communicated, etc. The spurious event may be characterized and/or identified, for example, as corresponding with a cap from a vial rather than a vial itself, as being a sensor error, etc., though such characterization and/or identification is not necessarily required for all embodiments. Typically though not necessarily, spurious events may be considered in evaluating overall performance of a bin/system and/or of a user taking a medication (or performing some similar action); for example, regardless of whether vials are detected to be deposited and/or when, it may be illuminating to note whether other materials are deposited and/or when, whether sensor errors are taking place and/or when, and so forth. Such spurious events may be considered with regard to determining adherence correspondence (see below), and/or for other purposes.

Still with reference to FIG. 15, a determination is made 1528 regarding adherence correspondence to a regimen. For example, the number and timing of contextual events, and/or the number and timing of spurious events, may be compared against a specified regimen for a medication, so as to provide some measure of adherence to that regimen. The adherence correspondence is also registered 1530.

Figure 16:
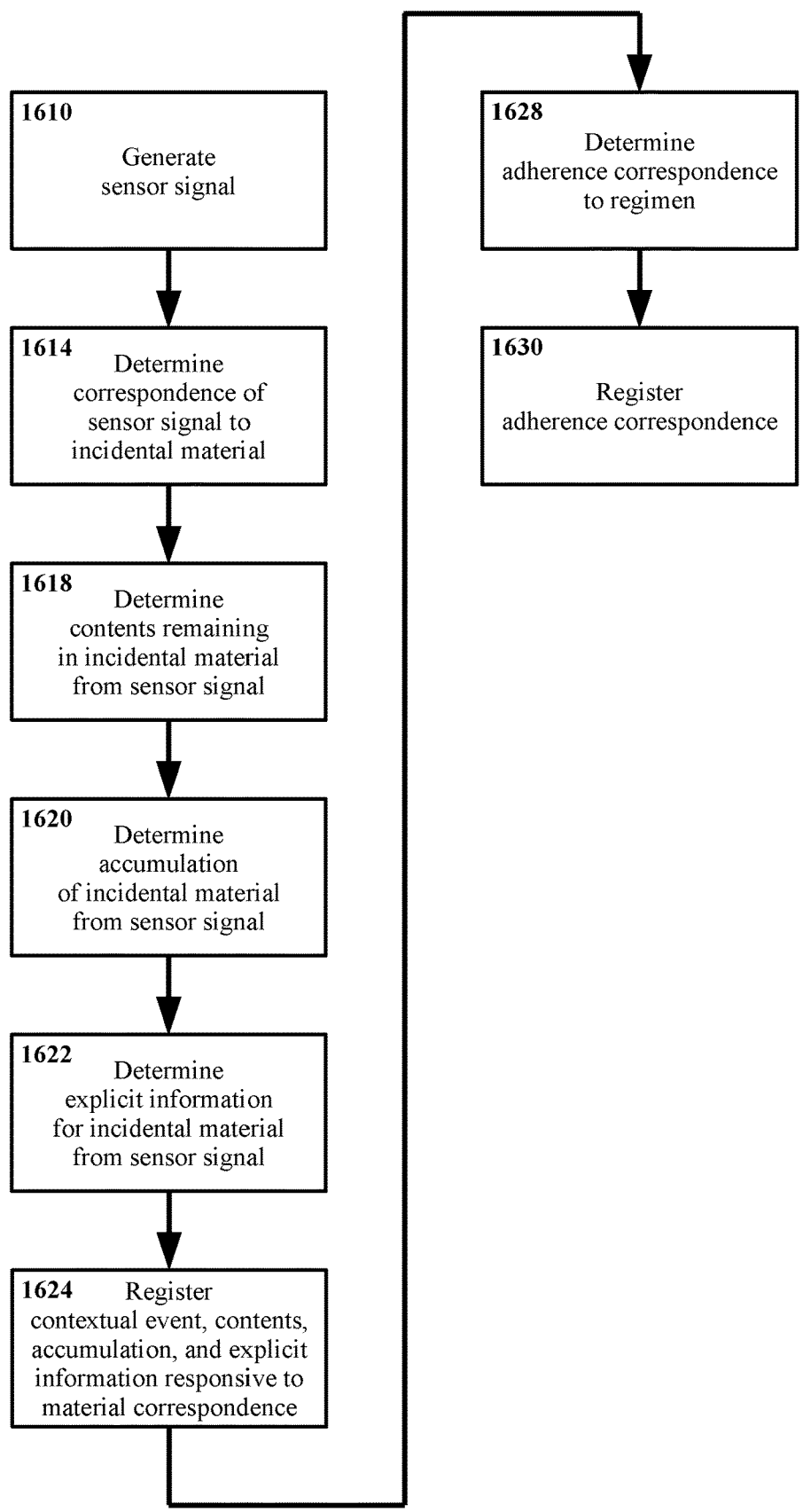
FIG. 16 shows an example method for smart authentication of medication use through considering non-smart incidental materials associated therewith, exhibiting supplemental data, in flow-chart form.

With reference to FIG. 16, another variation is shown, with attention to determining information other than correspondence of a sensor signal to the deposition of incidental material (or some other contextual event). Sensor data (whether from a single sensor and/or type of sensor, or from multiple sensors and/or sensor types) may be evaluated to determine a range of information, and is not limited only to determinations directly regarding contextual events.

In FIG. 16, at least one sensor signal is generated 1610, and a determination is made 1614 regarding the correspondence of the sensor signal to incidental material as deposited in a bin.

In addition, the sensor signal also is considered in determining 1618 how much of the contents of the incidental material remains therein at the time the incidental material is deposited. For example, a sensor signal from a light beam sensor may be evaluated to determine whether there is residual medication present in a vial passing through the light beam thereof, to determine at least approximately how much residual medication remains, etc. Alternately, a signal from an impact sensor may enable determination of how much contents remains in a container based on the impact force (e.g., if the weight of an empty container and the drop distance is known). As another example, a signal from a capacitive sensor may facilitate a determination of whether a blister pack deposited in a bin still has the pill therein, whether the blister pack remains sealed with foil, etc. based on measured variations in capacitance.

The sensor signal (and/or one of multiple sensor signals) is considered in determining 1620 an accumulation of incidental material within the bin. For example, a force sensor in the bottom of a bin may provide a signal indicating the total weight of vials deposited therein, such that if the weight of one empty vial is known the total number of empty vials may be determined. Alternately, a light beam sensor may indicate how many total vials are present within the bin based on how much a light beam is obstructed (or refracted, otherwise affected, etc.), while an imaging sensor may provide an image as may be evaluated to determine at least the approximate number of empty vials depicted therein.

The sensor signal may be considered in determining 1622 explicit information. For purposes of the example shown in FIG. 16, explicit information may be considered to include information that is explicitly added to the vial (or other incidental material), such as a bar code, printing, etched or stamped lettering, holographic foil images, magnetic stripes, etc. Such information may be understood as explicit at least in that typically bar codes, printing, etc. may be added to a vial or other material specifically to provide that information. For example, although residual medication may be detected within a used vial, typically that medication may not be placed in the vial to be detected but rather may be placed in the vial to be used. By contrast, explicit information in the form of a printed label applied to that vial may be provided specifically to be read or at least to be readable. It is noted that it is not required that explicit information be provided for the bin and/or sensors thereof in order to be detected by the bin and or sensors thereof; while dedicated printing applied specifically for detection by bin sensors is not prohibited, in practice explicit information may be acquired from labels as may be provided for other purposes, such as to identify the contents of a vial to the patient using the medication therein.

Other determinations may be made and/or information gathered from sensor signals, in addition to or instead of the examples presented. For instance, at least in principle it may be possible to identify a fingerprint on material deposited within a bin (e.g., through imaging at suitable wavelengths). In such instance, such a fingerprint may be compared against prints for the intended user of the medication (or other product) associated with that incidental material, as an indication of who is handling the material being deposited. Other arrangements also may be suitable.

Continuing in FIG. 16, the contextual event is registered 1624 (e.g., responsive to a positive correspondence), and the residual contents, accumulated material, and explicit information also are registered 1624. A determination is made 1628 regarding adherence correspondence to a regimen. As noted in previous examples, the contextual event(s) may be considered in such determination 1628, e.g., is a container disposed of, is the container disposed of at the proper time, etc. In addition, for arrangements wherein supplemental information such as residual medication, accumulation, and explicit information are determined, any or all such supplemental information also may be considered in determining 1628 adherence correspondence. For example, if a medication regimen specifies that a certain amount of medication is to be used, it may be suitable to consider how much medication remains in a used container to determine whether the correct amount has been dispensed therefrom (e.g., has been used). As another example, explicit information may indicate whether a vial is from a current or outdated prescription (e.g., based on a prescription or expiration date), or other information as may be relevant to determining adherence.

Regardless of the manner in which adherence correspondence is determined 1628, adherence correspondence is registered 1630. Supplemental information also may be registered therewith, and/or multiple factors of adherence, e.g., the user is taking the medication at the correct times but in the wrong dose, the user is taking medication correctly but is using medication that is expired, etc. Other information also may be registered.

Figure 17:
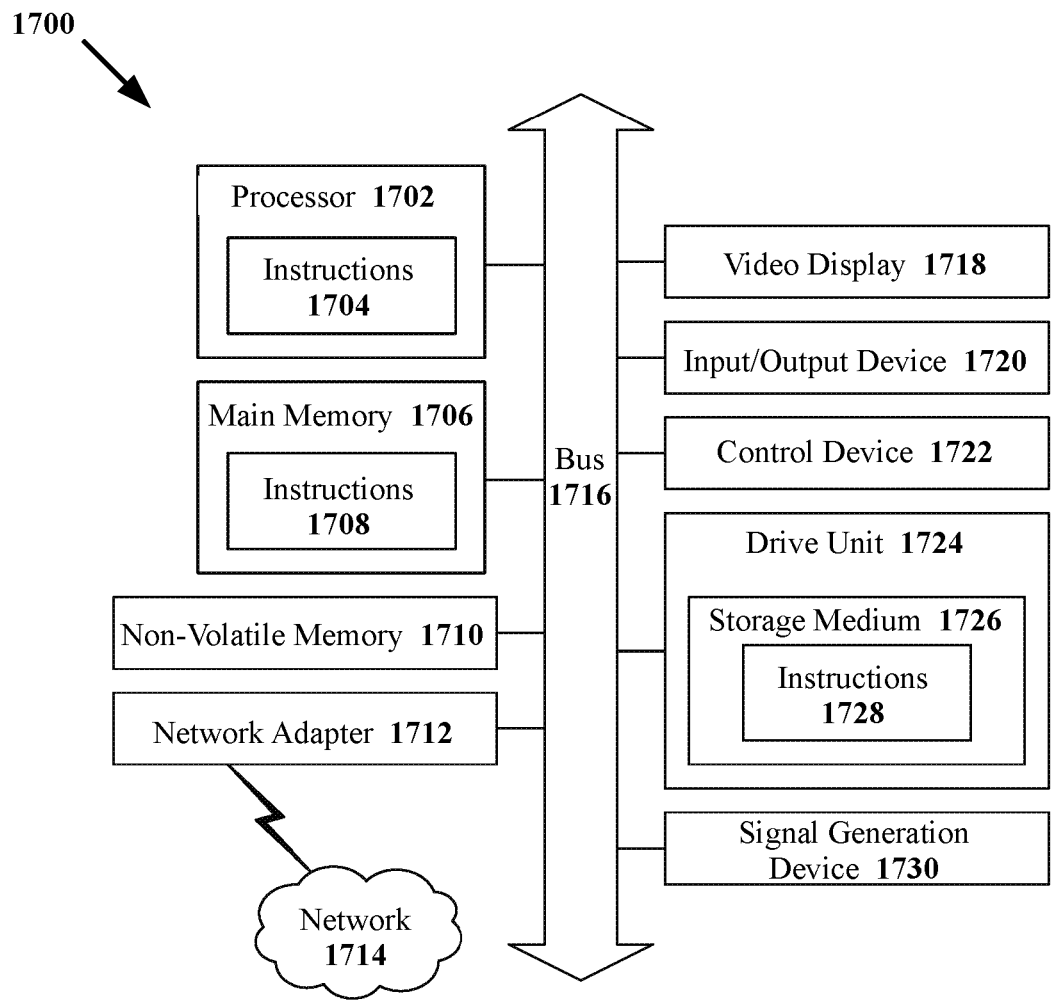
FIG. 17 is a block diagram illustrating an example of a processing system in which at least some operations described herein can be implemented.

FIG. 17 is a block diagram illustrating an example of a processing system 1700 in which at least some operations described herein can be implemented. The processing system may include one or more central processing units ("processors") 1702, main memory 1706, non-volatile memory 1710, network adapter 1712 (e.g., network interfaces), video display 1718, input/output devices 1720, control device 1722 (e.g., keyboard and pointing devices), drive unit 1724 including a storage medium 1726, and signal generation device 1730 that are communicatively connected to a bus 1716. The bus 1716 is illustrated as an abstraction that represents any one or more separate physical buses, point to point connections, or both connected by appropriate bridges, adapters, or controllers. The bus 1716, therefore, can include, for example, a system bus, a Peripheral Component Interconnect (PCI) bus or PCI-Express bus, a Hyper-Transport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

In various embodiments, the processing system 1700 operates as a standalone device, although the processing system 1700 may be connected (e.g., wired or wirelessly) to other machines. For example, in some embodiments components of the processing system 1700 are housed within a computer device used by a user to access an interface having skin care products or skin care regimens, while in other embodiments components of the processing system 1700 are housed within a network-connected container that holds one or more skin care products. In a networked deployment, the processing system 1700 may operate in the capacity of a server or a client machine in a client-server network environment, or as a peer machine in a peer-to-peer (or distributed) network environment.

The processing system 1700 may be a server, a personal computer (PC), a tablet computer, a laptop computer, a personal digital assistant (PDA), a mobile phone, a processor, a telephone, a web appliance, a network router, switch or bridge, a console, a hand-held console, a (hand-held) gaming device, a music player, any portable, mobile, hand-held device, or any machine capable of executing a set of instructions (sequential or otherwise) that specify actions to be taken by the processing system.

While the main memory 1706, non-volatile memory 1710, and storage medium 1726 (also called a "machine-readable medium) are shown to be a single medium, the term "machine-readable medium" and "storage medium" should be taken to include a single medium or multiple media (e.g., a centralized or distributed database, and/or associated caches and servers) that store one or more sets of instructions 1728. The term "machine-readable medium" and "storage medium" shall also be taken to include any medium that is capable of storing, encoding, or carrying a set of instructions for execution by the processing system and that cause the processing system to perform any one or more of the methodologies of the presently disclosed embodiments.

In general, the routines executed to implement the embodiments of the disclosure, may be implemented as part of an operating system or a specific application, component, program, object, module or sequence of instructions referred to as "computer programs." The computer programs typically comprise one or more instructions (e.g., instructions 1704, 1708, 1728) set at various times in various memory and storage devices in a computer, and that, when read and executed by one or more processing units or processors 1702, cause the processing system 1700 to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices 1710, floppy and other removable disks, hard disk drives, optical disks (e.g., Compact Disk Read-Only Memory (CD ROMS), Digital Versatile Disks, (DVDs)), and transmission type media such as digital and analog communication links.

The network adapter 1712 enables the processing system 1700 to mediate data in a network 1714 with an entity that is external to the computing device 1700, through any known and/or convenient communications protocol supported by the processing system 1700 and the external entity. The network adapter 1712 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1712 can include a firewall that can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including for example, the access and operation rights of an object by an individual, a machine, and/or an application, and the circumstances under which the permission rights stand.

As indicated above, the computer-implemented systems introduced here can be implemented by hardware (e.g., programmable circuitry such as microprocessors), software, firmware, or a combination of such forms. For example, some computer-implemented systems may be embodied entirely in special-purpose hardwired (i.e., non-programmable) circuitry. Special-purpose circuitry can be in the form of, for example, application-specific integrated circuits (ASICs), programmable logic devices (PLDs), field-programmable gate arrays (FPGAs), etc.

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

What is claimed is:

1. A method, comprising:
    instantiating a regimen standard for a medication regimen on a processor engaged with a bin;
    instantiating a container sensing standard on said processor;
    receiving a used single-dose medication container in said bin, via a chute of said bin;
    generating a first sensor signal, a second sensor signal, and a third sensor signal from respective first, second, and third light-beam sensors engaged with said chute, said sensors being configured such that light beams thereof are interrupted sequentially by said container in passing through said chute;
    communicating said sensor signals to said processor;
    in said processor, determining a container correspondence state of said sensor signals with said container sensing standard;
    in response to determining a positive container correspondence state, registering with said processor a medication container disposal event and an event time therefor, comprising:
        recording said event and said event time in a data store of said bin;
        communicating said event and said event time to an external entity via a wireless communicator of said bin;
        presenting said event and said event time via a graphical display of said bin;
    in said processor, determining an adherence correspondence state of said event and said event time to said regimen standard;
    registering said adherence correspondence state, comprising:
        recording said adherence correspondence state in said data store;
        communicating said adherence correspondence state to said external entity; and
        presenting said adherence correspondence state via said display.

2. A method, comprising:
    receiving an incidental material associated with a medication in a bin;
    detecting with a sensor said incidental material in said bin, and generating a sensor signal indicative thereof;
    communicating said sensor signal to a processor;
    in said processor, identifying said sensor signal as being consistent with said incidental material in said bin;
    in response to identifying said sensor signal as consistent, registering in said processor a contextual event and a contextual event time;
    determining from said contextual event and contextual event time an adherence to a regimen for said medication.

3. The method of claim 1, wherein:
    said incidental material comprises at least one of a container for said medication, packaging for said medication, a delivery implement for said medication, an unused portion of said medication, and a marker for said medication.

4. The method of claim 1, wherein:
    said incidental material comprises at least a portion of a single-use eye drop vial.

5. The method of claim 1, wherein:
    receiving said incidental material comprises said incidental material passing through a bin lid of said bin into a bin body of said bin.

6. The method of claim 1, wherein:
    detecting said incidental material in said bin comprises detecting an entry of said incidental material into said bin.

7. The method of claim 5, wherein:
    detecting said incidental material in said bin comprises detecting a passage of said incidental material through said bin lid into said bin body.

8. The method of claim 7, wherein:
    detecting said incidental material in said bin comprises optically detecting a presence of said incidental material within said bin lid.

9. The method of claim 8, wherein:
detecting said incidental material in said bin comprises optically detecting a motion of said incidental material through said bin lid.

10. The method of claim 1, wherein:
detecting said incidental material comprises at least one of light beam detection, optical image detection, capacitive detection, inductive detection, ultrasonic motion detection, impact detection, weight detection, and acoustic detection.

11. The method of claim 1, comprising:
detecting said incidental material in said bin with a plurality of sensors and generating a plurality of sensor signals indicative thereof.

12. The method of claim 1, wherein:
said processor comprises a cloud processor.

13. The method of claim 1, comprising:
communicating said contextual event and contextual time to an entity external to said bin; and
determining said adherence externally from said bin.

14. The method of claim 13, comprising:
determining said adherence in a cloud processor.

15. An apparatus, comprising:
a bin adapted to receive therein an incidental material associated with a medication;
at least one sensor adapted to sense said incidental material in said bin and to generate a sensor signal indicative thereof;
a processor in communication with said sensor, said processor being adapted to:
  identify said sensor signal as being consistent with said incidental material in said bin;
  register a contextual event and a contextual event time in response to identifying said sensor signal as consistent;
  determine from said contextual event and contextual event time an adherence to a regimen for said medication.

16. The apparatus of claim 15, wherein:
said bin comprises a bin body and a bin lid removably engaged with said bin body;
said bin body is adapted to accumulate said incidental material therein;
said bin lid is adapted to pass said incidental material therethrough to said bin body;
said sensor and said processor are engaged with said bin lid so as to be removable therewith from said bin body.

17. An apparatus, comprising:
a bin lid adapted to removably engage with a bin body, and adapted to pass an incidental material associated with a medication therethrough to said bin body;
at least one sensor adapted to sense said incidental material in said bin and to generate a sensor signal indicative thereof, said sensor being engaged with said bin lid;
a processor in communication with said sensor and engaged with said bin lid, said processor being adapted to:
  identify said sensor signal as being consistent with said incidental material in said bin body;
  register a contextual event and a contextual event time in response to identifying said sensor signal as consistent;
  determine from said contextual event and contextual event time an adherence to a regimen for said medication.

18. The apparatus of claim 17, wherein:
said bin lid defines an aperture therethrough, said sensor being in communication therewith so as to sense said incidental material therein.

19. The apparatus of claim 17, wherein:
said sensor is adapted to sense said incidental material without active signaling by said incidental material.

20. The apparatus of claim 17, wherein:
said sensor is adapted to sense said incidental material without sensor targets on said incidental material.

21. The apparatus of claim 17, wherein:
said sensor comprises at least one of a light beam sensor, an optical imager, a capacitance sensor, an inductive sensor, an ultrasonic sensor, an impact sensor, a weight sensor, and an acoustic sensor.

22. The apparatus of claim 17, comprising:
a plurality of sensors.

23. The apparatus of 18, comprising:
a plurality of sensors.

24. The apparatus of claim 18, comprising:
first, second, and third light beam sensors in communication with said aperture;
said first, second, and third light beam sensors being disposed at first, second, and third orientations with respect to said aperture; and
said first, second, and third light beam sensors being disposed at first, second, and third depths of said aperture.

25. An apparatus, comprising:
means for receiving an incidental material associated with a medication;
means for detecting said incidental material in a bin, and generating a signal indicative thereof;
means for identifying said signal as being consistent with said incidental material;
means for registering a contextual event and a contextual event time in response to identifying said signal as consistent;
means for determining from said contextual event and contextual event time an adherence to a regimen for said medication.

* * * * *